US010746981B2

(12) United States Patent
Tomer et al.

(10) Patent No.: US 10,746,981 B2
(45) Date of Patent: Aug. 18, 2020

(54) METHODS AND DEVICES FOR IMAGING LARGE INTACT TISSUE SAMPLES

(71) Applicant: The Board of Trustees of the Leland Stanford Junior University, Stanford, CA (US)

(72) Inventors: Raju Tomer, Palo Alto, CA (US); Karl A. Deisseroth, Stanford, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

(21) Appl. No.: 15/120,716

(22) PCT Filed: May 28, 2015

(86) PCT No.: PCT/US2015/032951
§ 371 (c)(1),
(2) Date: Aug. 22, 2016

(87) PCT Pub. No.: WO2015/184124
PCT Pub. Date: Dec. 3, 2015

(65) Prior Publication Data
US 2017/0068086 A1 Mar. 9, 2017

Related U.S. Application Data

(60) Provisional application No. 62/005,703, filed on May 30, 2014.

(51) Int. Cl.
*G02B 21/36* (2006.01)
*H04N 5/232* (2006.01)
(Continued)

(52) U.S. Cl.
CPC ....... *G02B 21/367* (2013.01); *G01N 33/4833* (2013.01); *G02B 21/008* (2013.01);
(Continued)

(58) Field of Classification Search
None
See application file for complete search history.

(56) References Cited

U.S. PATENT DOCUMENTS

| 3,129,158 A | 4/1964 | Raymond et al. |
| 3,208,929 A | 9/1965 | Raymond et al. |

(Continued)

FOREIGN PATENT DOCUMENTS

| CN | 102455501 | 5/2012 |
| CN | 103513411 A | 1/2014 |

(Continued)

OTHER PUBLICATIONS

Fahrbach et al., "Rapid 3D Light-Sheet Microscopy with a Tunable Lens," Optics Express, Sep. 9, 2013, pp. 21010-21026.*
(Continued)

*Primary Examiner* — Christopher Braniff
(74) *Attorney, Agent, or Firm* — Edward J. Baba; Michael J. Blessent; Bozicevic, Field & Francis LLP

(57) ABSTRACT

Methods and devices for conducting high-speed, high-resolution imaging of large intact tissue samples are provided. Aspects of the methods include placing a sample in an optically homogenous sample manipulation component, performing a calibration procedure to align a light sheet and a detection focal plane at a plurality of locations within the sample, and performing an imaging procedure on the sample to collect an image from each location. The collected images are reconstructed to form a three-dimensional image of the sample. Devices for carrying out the steps of the methods are also provided.

23 Claims, 14 Drawing Sheets

(51) Int. Cl.
*H04N 5/225* (2006.01)
*G02B 21/00* (2006.01)
*G02B 21/26* (2006.01)
*G01N 33/483* (2006.01)
*G02B 21/10* (2006.01)

(52) U.S. Cl.
CPC ..... *G02B 21/0032* (2013.01); *G02B 21/0076* (2013.01); *G02B 21/10* (2013.01); *G02B 21/26* (2013.01); *H04N 5/2256* (2013.01); *H04N 5/23212* (2013.01)

(56) References Cited

U.S. PATENT DOCUMENTS

| | | | |
|---|---|---|---|
| 3,346,479 | A | 10/1967 | Natelson |
| 3,375,187 | A | 3/1968 | Buchler |
| 3,563,880 | A | 2/1971 | Anderson |
| 3,576,727 | A | 4/1971 | Evatt |
| 3,616,454 | A | 10/1971 | Levy et al. |
| 3,616,457 | A | 10/1971 | Hjerten et al. |
| 3,674,678 | A | 7/1972 | Post et al. |
| 3,865,712 | A | 2/1975 | Davies |
| 3,989,613 | A | 11/1976 | Gritzner |
| 4,088,561 | A | 5/1978 | Anderson |
| 4,151,065 | A | 4/1979 | Kaplan et al. |
| 4,292,161 | A | 9/1981 | Hoefer et al. |
| 4,339,327 | A | 7/1982 | Tyler |
| 4,375,401 | A | 3/1983 | Catsimpoolas |
| 4,415,418 | A | 11/1983 | Turre et al. |
| 4,479,861 | A | 10/1984 | Hediger |
| 4,588,491 | A | 5/1986 | Kreisher et al. |
| 4,685,025 | A | 8/1987 | Carlomagno |
| 5,451,500 | A | 9/1995 | Stapleton |
| 5,475,429 | A * | 12/1995 | Kodama .......... G02B 7/365 348/350 |
| 6,219,575 | B1 | 4/2001 | Nemati |
| 6,232,092 | B1 | 5/2001 | Rogers |
| 6,472,216 | B1 | 10/2002 | Chiang |
| 6,722,395 | B2 | 4/2004 | Overbeck et al. |
| 7,660,620 | B2 | 2/2010 | Zeijlemaker et al. |
| 8,852,614 | B2 | 10/2014 | Frank et al. |
| 2004/0137613 | A1 | 7/2004 | Vacanti et al. |
| 2004/0267362 | A1 | 12/2004 | Hwang et al. |
| 2005/0047640 | A1* | 3/2005 | Eisfeld .......... G06K 9/00127 382/133 |
| 2005/0119736 | A1 | 6/2005 | Zilla et al. |
| 2005/0130317 | A1 | 6/2005 | Ventzki et al. |
| 2005/0181973 | A1 | 8/2005 | Genove et al. |
| 2005/0256588 | A1 | 11/2005 | Sawa et al. |
| 2007/0134798 | A1 | 6/2007 | McCormick et al. |
| 2008/0124374 | A1 | 5/2008 | Freyman |
| 2010/0055733 | A1 | 3/2010 | Lutolf et al. |
| 2010/0134881 | A1 | 6/2010 | Lippert et al. |
| 2012/0081518 | A1 | 4/2012 | Liu et al. |
| 2012/0112069 | A1* | 5/2012 | Piltch .......... G01N 21/645 250/338.1 |
| 2012/0196320 | A1 | 8/2012 | Seibel et al. |
| 2013/0065030 | A1 | 3/2013 | Tallant et al. |
| 2013/0094755 | A1 | 4/2013 | Lippert et al. |
| 2014/0030192 | A1 | 1/2014 | Deisseroth et al. |
| 2014/0092376 | A1 | 4/2014 | Xu et al. |
| 2014/0099659 | A1* | 4/2014 | Keller .......... G01N 21/6486 435/29 |
| 2014/0220574 | A1 | 8/2014 | Tuschl et al. |
| 2015/0087001 | A1 | 3/2015 | Gradinaru et al. |
| 2015/0144490 | A1 | 5/2015 | Deisseroth et al. |
| 2015/0153560 | A1 | 6/2015 | Lippert et al. |
| 2015/0267251 | A1 | 9/2015 | Cai et al. |
| 2016/0290899 | A1 | 10/2016 | Deisseroth et al. |
| 2017/0068086 | A1 | 3/2017 | Tomer et al. |

FOREIGN PATENT DOCUMENTS

| | | |
|---|---|---|
| EP | 1438976 | 7/2004 |
| JP | H05030409 | 2/1993 |
| JP | 2003502649 | 1/2003 |
| JP | 2004347513 | 12/2004 |
| JP | 2008504045 | 2/2008 |
| JP | 2013506150 | 2/2013 |
| WO | WO 1999036559 | 7/1999 |
| WO | WO 2000017355 | 3/2000 |
| WO | WO 2000077293 | 12/2000 |
| WO | WO 2005062938 | 7/2005 |
| WO | WO 2007030012 | 3/2007 |
| WO | WO 2009022133 | 2/2009 |
| WO | 2010014244 | 2/2010 |
| WO | WO 2010030358 | 3/2010 |
| WO | WO 2011111876 | 9/2011 |
| WO | WO 2012103343 | 8/2012 |
| WO | WO 2013191274 | 12/2013 |
| WO | 2014005866 | 1/2014 |
| WO | 2014025392 | 2/2014 |
| WO | 2014056992 | 4/2014 |
| WO | WO 2012147965 | 7/2014 |
| WO | WO 2012161143 | 7/2014 |
| WO | 2014182528 | 11/2014 |
| WO | 2015041755 | 3/2015 |
| WO | WO 2015028453 | 3/2015 |
| WO | WO 2016023009 | 2/2016 |
| WO | WO 2016073941 | 5/2016 |
| WO | WO 2016117614 | 7/2016 |
| WO | WO 2016147812 | 9/2016 |
| WO | WO 2015022883 | 3/2017 |
| WO | WO2017096248 | 6/2017 |

OTHER PUBLICATIONS

Zeiss, "Zeiss Lightsheet Z.1 Sample Preparation," Zeiss, Sep. 2013.*
Bouchard et al., "Swept Confocally-Aligned Planar Excitation (SCAPE) Microscopy for High Speed Volumetric Imaging of Behaving Organisms," Nat. Photonics. Feb. 2015. (Year: 2015).*
Fahrbach et al. (2013) "Rapid 3D light-sheet microscopy with a tunable lens" Optics Express 21(18):21010-21026.
Tomer and Deisseroth (2014). "Advanced Clarity Methods for Rapid and High-Resolution Imaging of Intact Tissues." pp. 37-44.
Zaber (2013) "Three-Axis Stages with Built in Controllers" Zaber Technologies Inc., pp. 1-3.
Zeiss (2013) "Zeiss Lightsheet Z.1 Sample Preparation." pp. 1-33.
Ackerly et al. (2000) "Glutamate slows axonal transport of neurofilaments in transfected neurons" *J Cell Biol* 150(1):165-176.
Albrecht et al. (2005) "Photo- and Electropatterning of Hydrogel-Encapsulated Living Cell Arrays" *Lab Chip* 5:111-118.
Bergen et al. (2008) "Nonviral Approaches for Neuronal Delivery of Nucleic Acids" *Pharm Res* 25(5):983-998.
Bevis and Glick (2002) "Rapidly maturing variants of the Discosoma red fluorescent protein (DsRed)" *Nature Biotechnology* 20:83-87.
Bouard et al. (2009) "Viral vectors: from virology to transgene expression" *British journal of pharmacology* 157(2):153-165.
Davidson and Breakefield (2003) "Viral vectors for gene delivery to the central nervous system" *Nat Rev Neurosci* 4(5):353-364.
Dodt et al. (2007) "Ultramicroscopy: three-dimensional visualization of neuronal networks in the whole mouse brain" *Nat Methods* 4(4):331-336.
Elsabahy et al. (2011) "Non-viral nucleic acid delivery: key challenges and future directions" *Curr Drug Deliv* 8(3):235-244.
Ertürk et al. (2012) "Three-dimensional imaging of solvent-cleared organs using 3DISCO" *Nature Protocols;* 7(11):1983-1995.
Ertürk et al. (2012) "Three-Dimensional Imaging of the Unsectioned Adult Spinal Cord to Assess Axon Regeneratoin and Glial Reponses after Injury" *Nature Medicine* 18(1):166-171.
Fletcher et al. (2010) "Cell mechanics and cytoskeleton" *Nature* 463(7280):485-492.
Giacca (2010) "Gene therapy" Dordrecht ; New York: Springer pp. 1-303.
Gradinaru et al. (2009) "Optical Deconstruction of Parkinsonian Neural Circuitry" Science 324(5925):354-359.
Hern and Hubbell (1998) "Incorporation of adhesion peptides into nonadhesive hydrogels useful for tissue resurfacing" *J. Biomed. Mater. Res.* 39(2):266-276.

(56) References Cited

OTHER PUBLICATIONS

Huh and Bae (1999) "Synthesis and characterization of poly(ethylene glycol)/poly(l-lactic acid) alternating multiblock copolymers" *Polymer* 40(22):6147-6155.
Jäderstad et al. (2010) "Communication via gap junctions underlies early functional and beneficial interactions between grafted neural stem cells and the host" *Proc Natl Acad Sci USA* 107(11):5184-5189.
Lee et al. (2010) "Hydrophobic nanoparticles improve permeability of cell-encapsulating poly(ethylene glycol) hydrogels while maintaining patternability" *PNAS USA* 107(48):20709-20714.
Ma et al. (2005) "Potential of Nanofiber Matrix as Tissue-Engineering Scaffolds" *Tissue Eng* 11(1-2)101-109.
Matz et al. (1999) "Fluorescent proteins from nonbioluminescent *Anthozoa* species" *Nature Biotechnology* 17: 969-973.
McLean et al. (2014) "Widespread neuron-specific transgene expression in brain and spinal cord following synapsin promoter-driven AAV9 neonatal intracerebroventricular injection" *Neurosci Lett* 576:73-78.
Nagai et al. (2002) "A variant of yellow fluorescent protein with fast and efficient maturation for cell-biological applications" *Nature Biotechnology* 20(1):87-90.
Nguyen and Daugherty (2005) "Evolutionary optimization of fluorescent proteins for intracellular FRET" *Nature Biotechnology* 23(3):355-360.
Oosthuysen et al. (2006) "Bioprosthetic tissue preservation by filling with a poly (acrylamide) hydrogel" *Biomaterials* 27(9):2123-2130.
Papadakis et al. (2004) "Promoters and control elements: designing expression cassettes for gene therapy" *Curr Gene Ther* 4(1):89-113.
Rizzo (2004) "An improved cyan fluorescent protein variant useful for FRET" *Nature Biotechnology* 22(4):445-449.
Seddon et al. (2004) "Membrane proteins, lipids and detergents: not just a soap opera" *Biochimica et Biophysica Acta* 1666:105-117.
Shaner et al. (2005) "A guide to choosing fluorescent proteins" *Nature Methods* 102(12):905-909.
Shkrob et al. (2005) "Far-red fluorescent proteins evolved from a blue chromoprotein from Actinia equine" *Biochem J.* 392(Pt 3):649-654.
Turano (2012) "Role of Chitin in Alzheimer's disease: a new cytotoxic pathway" Dissertation submitted to University of Verona 74 pages.
Wang et al. (2004) "Evolution of new nonantibody proteins via iterative somatic hypermutation" *PNAS USA* 101(48):16745-16749.
West and Hubbell (1999) "Polymeric Biomaterials with Degradation Sites for Proteases Involved in Cell Migration" *Macromolecules* 32(1):241-244.
Wiedenmann et al. (2002) "A far-red fluorescent protein with fast maturation and reduced oligomerization tendency from *Entacmaea quadricolor (Anthozoa, Actinaria)*" *PNAS USA* 99(18):11646-11651.
Wittmer et al. (2009) "Silk Nanofibers for Biomaterials" *Material Research Society Conference* Session WW7: Polymer Nanofibers for Medicine and Biology I.
Zhang et al. (2006) "Viral vectors for gene delivery in tissue engineering" *Adv Drug Deliv Rev.* 58(4):515-534.
Zhang et al. (2010) "Optogenic interrogation of neural circuits: technology for probing mammalian brain structures" *Nat Protoc* 5(3):439-456.
Zheng et al. (2005) "Molecular cloning and functional characterization of mouse chitotriosidase" *Gene* 29:357(1):37-46.
Zhu et al. (2011) "Design properties of hydrogel tissue-engineering scaffolds" *Expert Rev Devices;* 8(5):607-626.
Flood et al. (2013) "ZEISS Lightsheet Z.1" School of Biology & Environmental Science, 1-34.
Barth et al. (2004) "Alteration of neuronal firing properties after in vivo experience in a FosGFP transgenic mouse" I Neurosci. 24, 6466-6475.
Battich et al. (2013) "Image-based transcriptomics in thousands of single human cells at single-molecule resolution" Nat Meth 1-10.

Bloodgood et al (2013) "The activity-dependent transcription factor NP AS4 regulates domainspecific Inhibition" Nature 503, 121-125.
Choi et al. (2014) "Next-Generation in Situ Hybridization Chain Reaction: Higher Gain, Lower Cost Greater Durability" ACS Nano 8, 4284-4294.
Choi et al. (2010) "Programmable in situ amplification for multiplexed imaging ofmRNA Expression" Nat. Biotechnol. 28, 1208-1212.
Chung et al. (2013) "Structural and molecular interrogation of intact biological systems" Nature 497, 332-337.
Ciafre et al. (2005) "Extensive modulation of a set of microRNAs in primary glioblastoma" Biochem. Biophys. Res. Commw1. 334, 1351-1358.
Denk et al. (2004) "Serial block-face scanning electron microscopy to reconstruct three-dimensional tissue nanostructure" PLoS Biol2, e329.
Dodt et al. (2007 "Ultramicroscopy: three-dimensional visualization of neuronal networks in the whole mouse brain". Nat Meth 4, 331-336.
Egen et al. (2012) "Three-dimensional imaging of solvent-cleared organs using 3D1SCO" Nature Protocols 7, 1983-1995.
Esteller et al. (2011). Non-coding RIT"As in human disease. Nat Rev Genet 12, 861-874.
Garner et al. (2012) "Generation of a synthetic memory trace" Science 335, 1513-1516.
Guenthner et al. (2013) "Permanent genetic access to transiently active neurons via TRAP: targeted recombination in active populations" Neuron 78, 773-784.
Guzowski et al. (1999) "Environment-specific expression of the immediate-early gene Arc in hippocampal neuronal ensembles" Nat Neurosci 2, 1120-1124.
Hama et al. (2011). Scale: a chemical approach for fluorescence imaging and reconstruction of transparent mouse brain. Nat Neurosci 14, 1481-1488.
Hama et al. (2015) "ScaleS: an optical dearing palette for biological imaging" Nat Neurosci 1-14.
Ke et al. (2013) "In situ sequencing for RNA analysis in preserved tissue and cells" Nat Meih 10, 857-860.
Kuwajima et al. (2013) "ClearT: a detergent- and solvent-free clearing method for neuronal and nonneuronal Tissue" Development 140, 1364-1368.
Landgraf et al. (2007) "A mammalian microRNA expression atlas based on small RNA library sequencing". Cell 129, 1401-1414.
Lee et al. (2014) "Highly Multiplexed Subcellular Rt\JA Sequencing in Situ" Science 343, 1360-1363.
Li et al. (2015) "Fast immune-labeling by electrophoretically driven infiltration for intact tissue imaging" Sci Rep 5, 10640.
Lin et al. (2011) "Functional identification of an aggression locus in the mouse hypothalamus" Nature 470, 221-226.
Lyford et al. (1995) "Arc, a growth factor and activity-regulated gene, encodes a novel cytoskeletonassociated protein that is enriched in neuronal dendrites" Neuron 14, 433-445.
Masuda et al. (1999) "Analysis of chemical modification of RNA from formalin-fixed samples and optimization of molecular biology applications for such samples" Nucleic Acids Research 27, 4436-4443.
Mattson et al. (1993) "A practical approach to crosslinking" Mol. Biol. Rep. 17, 167-183.
Nedivi E. (2009). The Function of Activity-Regulated Genes in the Nervous System. Physiological Reviews 89, 1079-1103.
Nedivi et al. (1993) "Numerous candidate plasticity-related genes revealed by differential eDNA cloning" Nature 363, 718-722.
Oh et al. (2014) "A mesoscale connectome of the mouse Brain" Nature 508, 207-214.
Pang et al. (2009) "Oncogenic role of microRNAs in brain tumors" Acta Neuropathol. 117, 599-611.
Pena et al. (2009) "miRNA in situ hybridization in formaldehyde and EDC-fixed tissues". Nat Meth 6, 139-141.
Ramirez et al. (2013) "Creating a false memory in the hippocampus" Science 34L 387-391.
Reijmers et al. (2007) "Localization of a stable neural correlate of associative memory" Science 317, 1230-1233.

(56) References Cited

OTHER PUBLICATIONS

Renier et al. (2014) "iDISCO: a simple, rapid method to immunolabel large tissue samples for volume Imaging". Cell 59, 896-910.
Renwick et al. (2013) "Multicolor microRNA FISH effectively differentiates tumor types". J. Clin. Invest. 123, 2694-2702.
Resch-Genger et al. (2008) "Quantum dots versus organic dyes as Fluorescent labels". Nat Meth 5, 763-775.
Richardson et al. (2015) Clarifying Tissue Clearing Cell 162, 246-257.
Shen et al. (2004) "X-ray photoelectron spectroscopy and infrared spectroscopy study of maleimide-activated supports for immobilization of oligodeoxyribonudeotides". Nucleic Acids Research 32, 5973-5980.
Sheng et al. (1990) "Membrane depolarization a.nd calcium induce c-fos transcription via phosphorylation of transcription factor CREB". Neuron 4, 571-582.
Simard et al. (2001) "Urea substitutes toxic formamide as destabilizing agent in nucleic acid hybridizations with RNA probes" Electrophoresis 22, 2679-2683.
Smeyne et al. (1992) "Fos-lacZ transgenic mice: mapping sites of gene induction in the central nervous system" Neuron 8, 13-23.
Song et al. (2012) "Hybridization chain reaction-based aptameric system for the highly selective and sensitive detection of protein". Analyst 137, 1396-1396.
Srinivasan et al. (2002) "Effect of fixatives and tissue processing on the content and integrity of nucleic acids" The American Journal of Pathology 161,1961-1971.
Staudt et al. (2007) "2,2'-thiodiethanol: a new water soluble mounting medium for high resolution optical Rnicroscopy" Microsc. Res. Tech. 70, 1-9.
Susaki et al. (2014) "Whole-brain imaging with single-cell resolution using chemical cocktails and computational analysis" Cell 157, 726-739.
Tainaka et al. (2014). "Whole-body imaging with single-cell resolution by tissue decolorization" Cell 159,911-924.
Tomer et al. (2014) "Advanced Clarity for rapid and high-resolution imaging of intact tissues" Nature Protocols 9, 1682-1697.
Tymianski et al. (1997) "A novel use for a carbodiimide compound for the fixation of fluorescent and non-tluorescent calcium indicators in situ following physiological experiments" Cell Calcium 21, 175-183.
Wanner et al. (2015). "Challenges of microtome-based serial block-face scanning electron microscopy in neuroscience" J Microsc 259, 137-142.
Wemersson et al. (2007) "Probe selection for DNA microarrays using OligoWiz" Nature Protocols 2, 2677-2691.
Yang et al. (2014) "Single-cell phenotyping within transparent intact tissue through whole-body clearing" Cell 158, 945-958.
Zeisel et al. (2015) "Cell types in the mouse cortex and hippocampus revealed by single-cell RNA-seq" Science 347, 1138-1142.
Zheng et al. (2015) "Simplified CLARITY for visualizing immunofluorescence labeling in the developing rat brain" Brain Struct Funct 1-9.
Zhou et al. (2009) "Evidence for selective microRNAs and their effectors as common long-term targets for the actions of mood stabilizers" Neuropsychopharmacology 34, 1395-1405.

\* cited by examiner

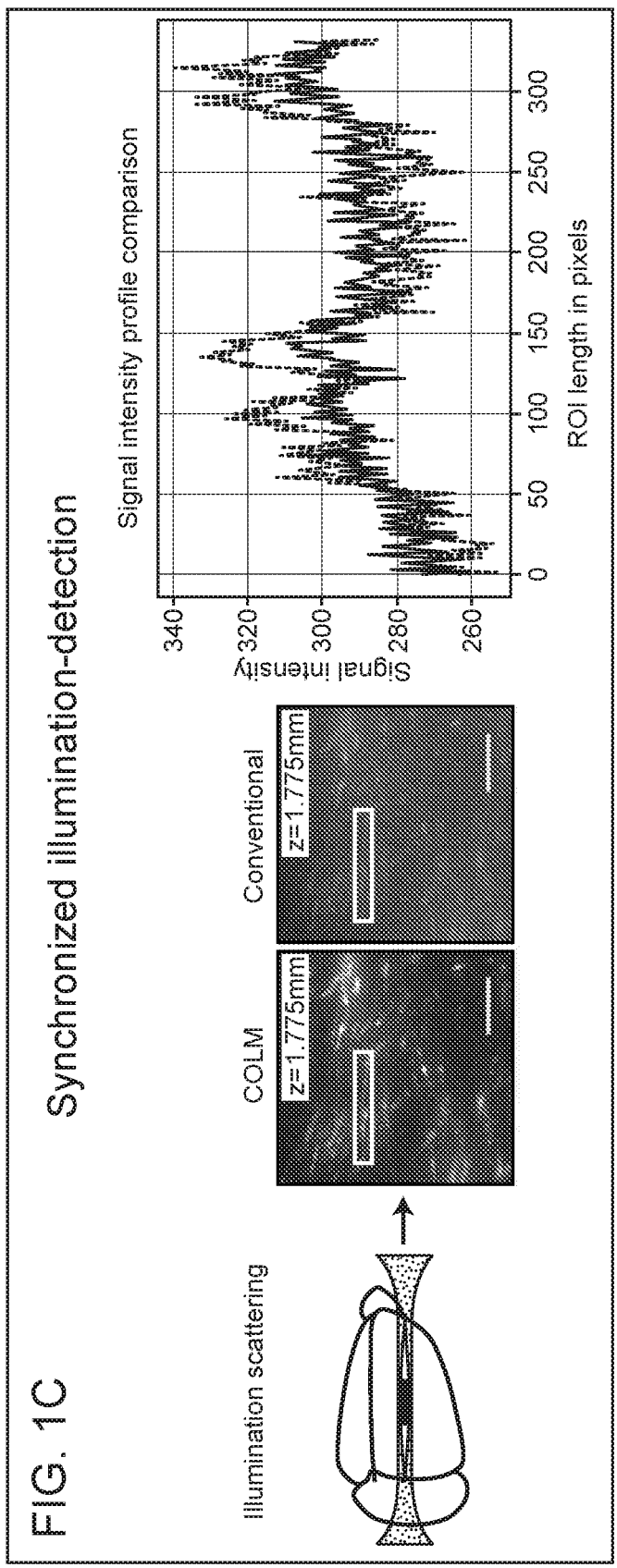
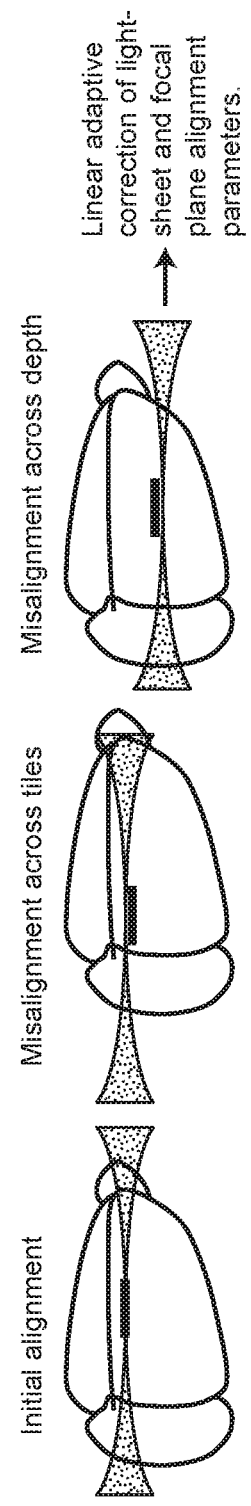
FIG. 1C
FIG. 1D

FIG. 6

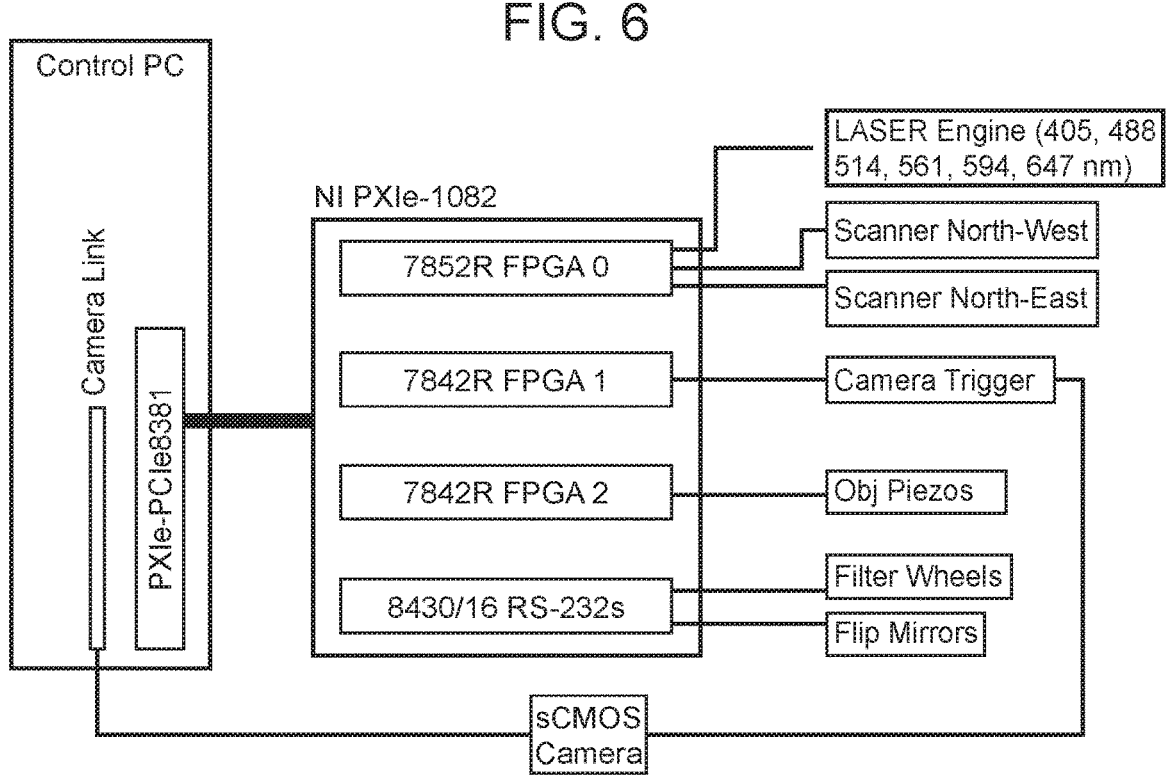

| COLM Parts | Vendor | Part number |
|---|---|---|
| LASER engine | Omicron | SOLE -6: 405, 488, 515, 561, 594, 647 nm |
| Camera | Hamamatsu | Orca Flash 4.0 V2 |
| Detection Objectives | Olympus | 10X/0.6 and 25X/0.95 CLARITY |
| Illumination Objectives | Olympus | Macro 4X/ 0.28 NA (Qty=2) |
| XYZ -theta sample stage | Physik Instrumente | M-112K033 ; M-116.DG (Qty=3) |
| Sample chamber | Custom design | Custom design |
| Illumination Filter Wheels + Smart hutter | Sutter | FG -LB10 -NWIQ (Qty=2) |
| Emission Filter Wheel | Sutter | FG - LB10 -W50 |
| Galvo XY Scanners | Cambridge Tech | 6215H XY mounted (Qty=2) |
| Tube lens | Thorlabs | ITL200 (Qty=3) |
| Scan lens | Sill Optics | S4LFT0061/065 (Qty=2) |
| Filters | Semrock | RazorEdge long pass and band pass filters |
| Sample holder cuvette | Starna Cells | Quartz cuvette |
| Sample holder adapter | Custom | Custom |
| FPGA | National Instruments | 7852R , 7842R (Qty=2) |
| PXI express chassis | National Instruments | PXIe - 1082 |
| Serial card | National Instruments | 8430/16 |
| Objective piezos | Physik Instrumente | Hera stages P -622.1CD (Qty=3) |

Summary of the control electronics framework and COLM parts. FPGA logic is used to control and synchronize various parts of the microscope.

FIG. 8 (Cont.)
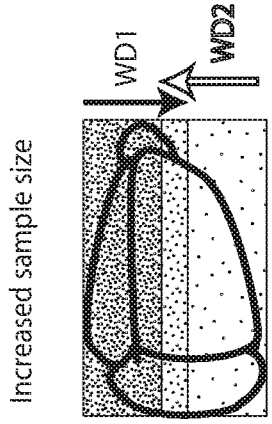
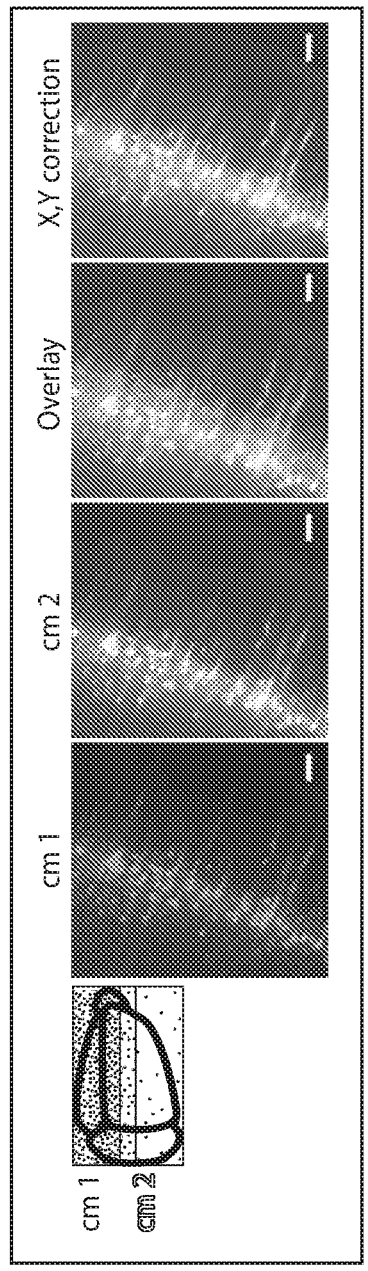

METHODS AND DEVICES FOR IMAGING LARGE INTACT TISSUE SAMPLES

CROSS REFERENCE TO RELATED APPLICATIONS

This application claims priority benefit of the filing date of U.S. Provisional Patent Application Ser. No. 62/005,703, filed on May 30, 2014, the disclosure of which application is herein incorporated by reference in its entirety.

INTRODUCTION

A major challenge to the imaging of large intact tissue samples is to conduct the imaging process in a practically feasible period of time. Confocal microscopes suffer from slow imaging speeds, and can also damage the signal-emitting capabilities of a sample due to photo-bleaching before the sample is completely imaged. There is a need in the art for high-speed, high-resolution imaging methods and devices that can be used to decrease the amount of time required to image a large tissue sample while minimizing the effects of photo-bleaching on the sample. The present invention addresses these and other needs.

SUMMARY

Methods and devices for conducting high-speed, high-resolution imaging of large intact tissue samples are provided. Aspects of the methods include placing a sample in an optically homogenous sample manipulation component, performing a calibration procedure to align a light sheet and a detection focal plane at a plurality of locations within the sample, and performing an imaging procedure on the sample to collect an image from each location. The collected images are reconstructed to form a complete three-dimensional image of the sample. Devices for carrying out the steps of the methods are also provided.

BRIEF DESCRIPTION OF THE DRAWINGS

The invention may be best understood from the following detailed description when read in conjunction with the accompanying drawings. Included in the drawings are the following figures:

FIGS. 1C and 1D show schematics for synchronized illumination detection and automated alignment parameter calibration in COLM. All scale bars: 100 µm.

FIG. 6 shows a schematic summary of the control electronics framework and COLM parts.

DETAILED DESCRIPTION

Figure 1A:
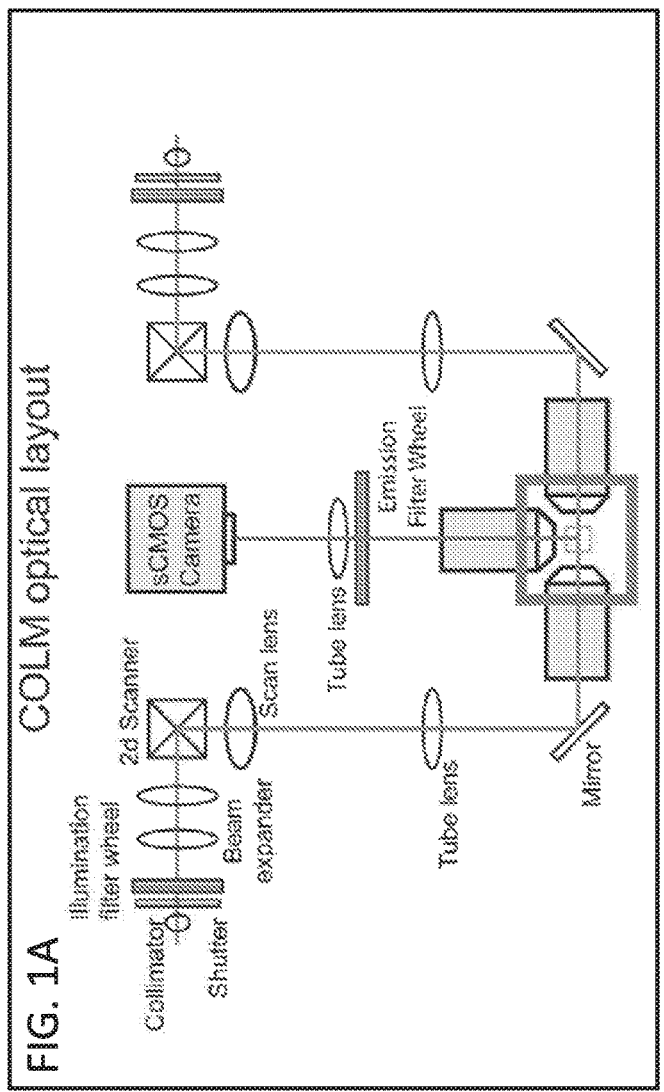
FIG. 1A shows an optical layout of a CLARITY optimized light-sheet microscope (COLM).

Methods and devices for conducting high-speed, high-resolution imaging of large intact tissue samples are provided. Aspects of the methods include placing a sample in an optically homogenous sample manipulation component, performing a calibration procedure to align a light sheet and a detection focal plane at a plurality of locations within the sample, and performing an imaging procedure on the sample to collect an image from each location. The collected images are reconstructed to form a three-dimensional image of the sample. Devices for carrying out the steps of the methods are also provided.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of embodiments of the invention in greater detail, aspects of the systems and devices of various embodiments are reviewed first in greater detail, followed by a discussion of methods and kits according to certain embodiments of the invention.

Systems

Aspects of the invention include systems and devices thereof configured for imaging large intact tissue samples. In some embodiments, the subject systems include a microscope device comprising an illumination beam path that comprises a light source, a detection beam path that comprises a camera, an optically homogenous sample manipulation component that comprises a sample chamber, a controller, a processor, and a computer-readable medium comprising instructions that, when executed by the processor, cause the controller to execute a calibration procedure to acquire a plurality of alignment parameters for a sample in the sample chamber, and execute an imaging procedure that utilizes the alignment parameters to generate a three dimensional image of the sample. Each of these components is now further described in greater detail.

As summarized above, aspects of the invention include systems that include an illumination beam path. Illumination beam path components are well known in the art and are not described in great detail herein. In some embodiments, illumination beam path components may include a collimator, shutter, illumination filter wheel, beam expander, two-dimensional scanner, scan lens, tube lens, one or more mirrors, and a light source, as described further below. Any of these components, or combinations or arrangements thereof, may be utilized in a suitable manner in the subject systems and devices.

In some embodiments, an illumination beam path includes a cylindrical lens that is configured to generate a static light sheet. In some embodiments, an illumination beam path includes galvanometer scanner/f-theta lens configured to create dynamic light sheets with a Gaussian or Bessel beams. In some embodiments, a system may include two illumination beam paths, wherein the illumination beam paths are configured to illuminate a sample from opposite or opposing sides of the sample.

In some embodiments, a system may be configured to generate a plurality of light sheets, such as one, two, three, four or more light sheets from a single illumination beam path. In certain embodiments, a light sheet can be independently manipulated to illuminate a desired portion of a sample. In some embodiments, two or more light sheets can be used to illuminate a portion of a sample in a coordinated manner, such that a first light sheet illuminates a first portion of the sample, and a second light sheet illuminates second portion of the sample, wherein the first portion of the sample is different from the second portion of the sample. In some embodiments, a plurality of light sheets can be used to illuminate a portion of a sample, for example, up to three or more, such as four or more, such as five or more, such as six or more, such as seven or more, such as eight or more light sheets can be used to illumination a portion of a sample in a coordinated manner. In some embodiments, each light sheet can be manipulated independently to illuminate a given portion of a sample. In some embodiments, a plurality of light sheets can be manipulated in a coordinated manner to accomplish imaging of a sample in accordance with the methods described further herein.

In some embodiments, a system may include two illumination beam paths. In certain embodiments, two illumination beam paths may be used to illuminate a sample from opposite sides, thereby allowing one half of the sample to be imaged from one side, and the other half of the sample to be imaged from another side.

Illumination beam paths in accordance with embodiments of the invention may also include various light sources configured to generate light in the visible spectrum, having a wavelength ranging from 390 to 700 nm, or in Infrared spectrum in sub-range 700-1500. In some embodiments, a light source may include a laser. In some embodiments, a light source (such as a laser light source) is configured to emit light having a wavelength of, e.g., 405 nm, 488 nm, 514 nm, 561 nm, 594 nm, or 647 nm. Any of a variety of suitable light sources may be used with the subject systems.

As summarized above, aspects of the invention include systems that include a detection beam path. Detection beam path components are well known in the art and are not described in great detail herein. In some embodiments, detection beam path components include a camera, tube lens, emission filter wheel, and a detection objective. Any of these components, or combinations or arrangements thereof may be utilized in a suitable manner in the subject systems and devices.

In some embodiments, a camera is a CCD camera or a scientific CMOS camera (sCMOS) providing extremely low noise, rapid frame rates, wide dynamic range, high quantum efficiency (QE), high resolution, and large field of view. Such cameras are commercially available from scientific technology vendors.

In some embodiments, a detection objective is configured to have a refractive index (RI) that matches the RI of a sample undergoing imaging. For example, in some embodiments, a detection objective may be a 25×, 10×, or 4× detection objective whose RI is matched with that of an immersion liquid and/or tissue sample undergoing imaging analysis.

In some embodiments, a detection objective may be a low numerical aperture detection objective. The numerical aperture of an objective describes how much of the emitted light signal (e.g., fluorescence signal) can be collected by the objective and the diffraction-limited resolution that can be achieved. Higher numerical aperture translates to improved resolution in wavelength-dependent fashion, according to the relationship defined by the Abbe diffraction limit of $\lambda/2NA$. In some embodiments, the numerical aperture of the detection objective ranges from 0.1 to 1.4, such as 0.6 to 1.0

In some embodiments, a detection objective has a working distance (WD), which is the distance between the focal plane (or imaging plane) and the physical edge of the objective lens. The WD of a detection objective therefore determines how deep into a sample imaging can be conducted without physical contact between the sample and the objective lens. In some embodiments, a WD of a detection objective ranges from 0.1 to 100 mm, such as 6-8 mm.

In some embodiments, a system may include two detection beam paths. In certain embodiments, two detection beam paths may be used to simultaneously image a sample from opposite sides, thereby allowing one half of the sample to be imaged from one side, and the other half of the sample to be imaged from another side. This embodiment provides a two-fold increase in the sample size that can be imaged, as the overall working distance of the combination of both objectives is increased by two fold through the addition of a second objective in the second detection beam path.

As summarized above, aspects of the invention include an optically homogenous sample manipulation component configured to contain a sample in an optically homogenous environment. By "optically homogenous" is meant that the refractive indeces (RIs) of the various materials in the environment are matched, or are similar, such that a beam of light traveling through the optically homogenous environment will be insubstantially impacted by any changes in the RIs of the materials through which it travels.

In some embodiments, the optically homogenous sample manipulation component comprises a bottom or base and an outer wall that defines a sample chamber in the shape of a box with an open top. In some embodiments, a lens from one or more illumination beam paths is disposed on or in a portion of the outer wall such that light emitted from an illumination beam path enters directly into an interior portion of the sample chamber via a transparent window. In some embodiments, the transparent window is made of a material that matches the RI of the optically homogenous environment. In some embodiments, the transparent window is made from, e.g., quartz coverslips. In some embodiments, a detection objective of a detection beam path is disposed on or in a portion of the outer wall. In some embodiments, a detection objective is positioned in an orthogonal relationship to an illumination beam path (e.g., is positioned at a 90° angle to an illumination beam path).

In some embodiments, the optically homogenous sample manipulation component includes an xyz-theta sample mount that is configured to move a sample in any of a plurality of directions, including x, y, and z directions as well as angular or rotational directions. In some embodiments, the xyz-theta stage mount has a large travel range and is configured to move at least 45 mm is each of the x, y, and z directions. In some embodiments, the xyz-theta stage mount is configured to rotate the sample by a full 360° in the angular or theta direction. Such xyz-theta sample mounts are commercially available from scientific technology vendors.

In some embodiments, the optics of the system are configured to move with respect to the sample, whereas in some embodiments, the sample manipulation component is configured to move the sample with respect to the optics of the system. Movement of either the optics or the sample manipulation components can be, e.g., in a step-by-step manner or in a continuous manner. In some embodiments, the optics and the sample manipulation components can be moved in a synchronous manner, whereas in certain embodiments, the optics and the sample manipulation components can be moved in an asynchronous manner.

In some embodiments, the sample chamber of the optically homogenous sample manipulation component is filled with a solution. In some embodiments, the solution has an RI that matches the RI of the sample or the detection objective of the detection beam path. For example, in some embodiments, the solution used to fill the sample chamber is FocusClear or MountClear (both commercially available from CelExplorer Labs). In some embodiments, the solution used to fill the chamber is a liquid with a refractive index that ranges from 1.42 up to 1.46, such as 1.45. In some embodiments, the solution used to fill the sample chamber is 87% glycerol. Solutions having the desired range of refractive indices are commercially available from vendors, such as Cargille Labs.

In some embodiments, the sample chamber of the optically homogenous sample manipulation component comprises a smaller inner chamber whose volume is less that the volume of the larger, outer sample chamber. For example, in some embodiments, the inner chamber is a cuvette that is configured to house a sample for analysis. In certain embodiments, a cuvette made from fused quartz is used as the inner chamber. In some embodiments, the inner chamber is filled with a solution, as described above, whose RI matches the RI of the sample or the detection objective of the detection beam path. For example, in some embodiments, the solution used to fill the inner chamber is FocusClear or MountClear (both commercially available from CelExplorer Labs). In some embodiments, the solution used to fill the inner chamber is RI 1.454, commercially available from vendors such as Cargille Labs. In some embodiments, the solution used to fill the inner chamber is 87% glycerol. In certain embodiments, a first solution may be used to fill the inner chamber, and a different solution may be used to fill the larger, outer chamber. For example, in some embodiments, the inner chamber is filled with FocusClear, while the outer chamber is filled with RI 1.454 solution, or 87% glyercol solution.

As summarized above, aspects of the invention include a controller, processor and computer readable medium that are configured or adapted to control or operate one or more components of the subject systems. In some embodiments, a system includes a controller that is in communication with one or more components of the systems, as described herein, and is configured to control aspects of the systems and/or execute one or more operations or functions of the subject systems. In some embodiments, a system includes a processor and a computer-readable medium, which may include memory media and/or storage media. Applications and/or operating systems embodied as computer-readable instructions on computer-readable memory can be executed by the processor to provide some or all of the functionalities described herein.

In some embodiments, a system includes a user interface, such as a graphical user interface (GUI), that is adapted or configured to receive input from a user, and to execute one or more of the methods as described herein. In some embodiments, a GUI is configured to display data or information to a user.

Referring now to FIG. 1A, an embodiment of a microscope device is depicted. The depicted microscope device includes a first and a second illumination beam path, wherein each illumination beam path includes a collimator, shutter, illumination filter wheel, beam expanders, 2d galvanometer scanner, scan lens (or f-theta lens), tube lens, mirror and illumination objective. The depicted microscope device also includes a detection beam path that includes an sCMOS camera, tube lens, emission filter wheel and a detection objective that is positioned within the optically homogenous sample manipulation component.

Figure 1B:
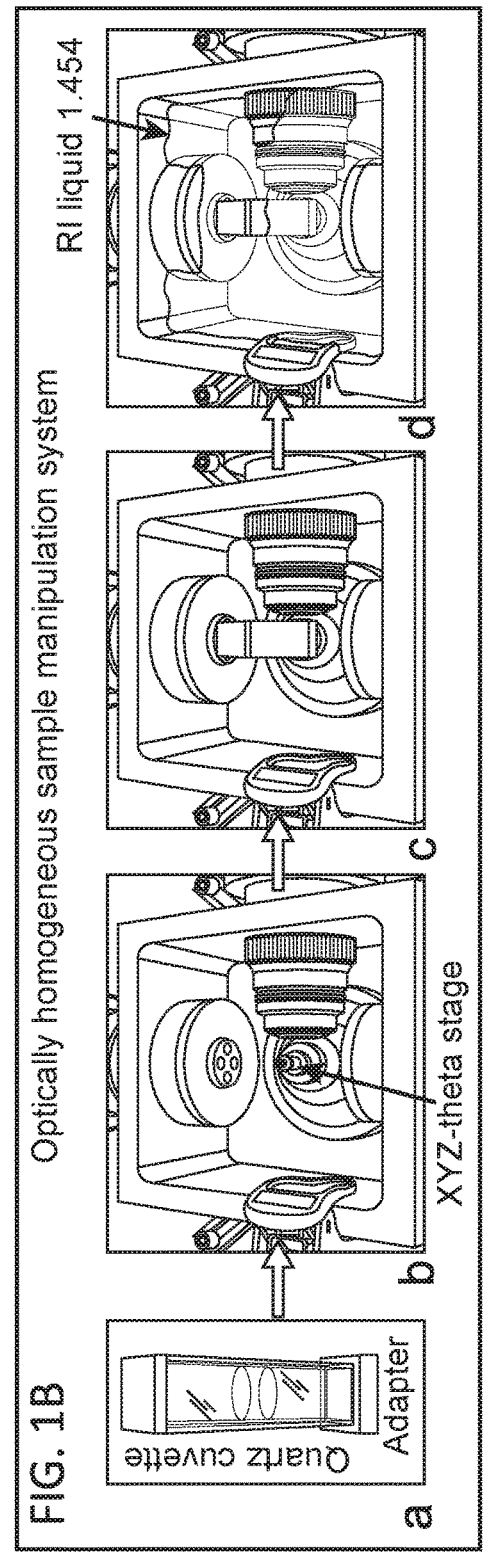
FIG. 1B, Panels a-d show an optically homogeneous sample mounting framework for large intact samples.

Referring now to FIG. 1B, various components of an optically homogenous sample manipulation component are depicted. Panel a shows a quartz cuvette that may serve as an inner sample chamber. Panel b shows an xyz-theta sample mount stage positioned on the base of the sample chamber. The detection objective of the detection beam path and the lenses of two illumination beam paths are also shown. Panel c shows the cuvette placed within the sample chamber to form an inner sample chamber. Panel d shows the sample chamber filled with RI 1.454 liquid.

Referring now to FIG. 6, a schematic summary of the control electronics framework and COLM parts are shown. As depicted, a control computer or processor communicates with the various components of the systems, including, e.g., an sCMOS camera in the detection beam path, a laser controller in the illumination beam path, and various additional components.

Figure 8:
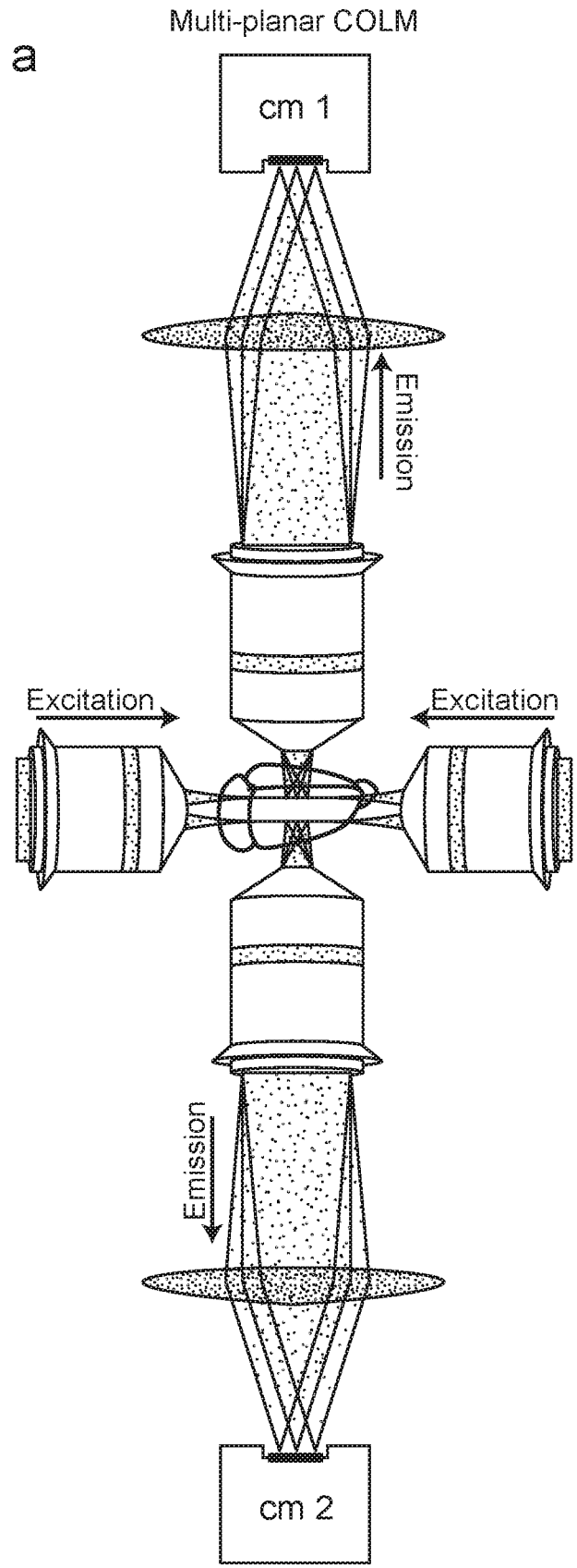
FIG. 8, Panel a shows a schematic representation of a multi-planar COLM having two illumination beam paths and two detection beam paths. Panels b and c show schematic representations of various imaging methods that can be carried out using the system depicted in Panel a, to achieve deeper imaging and increased imaging speed.
Figure 8:
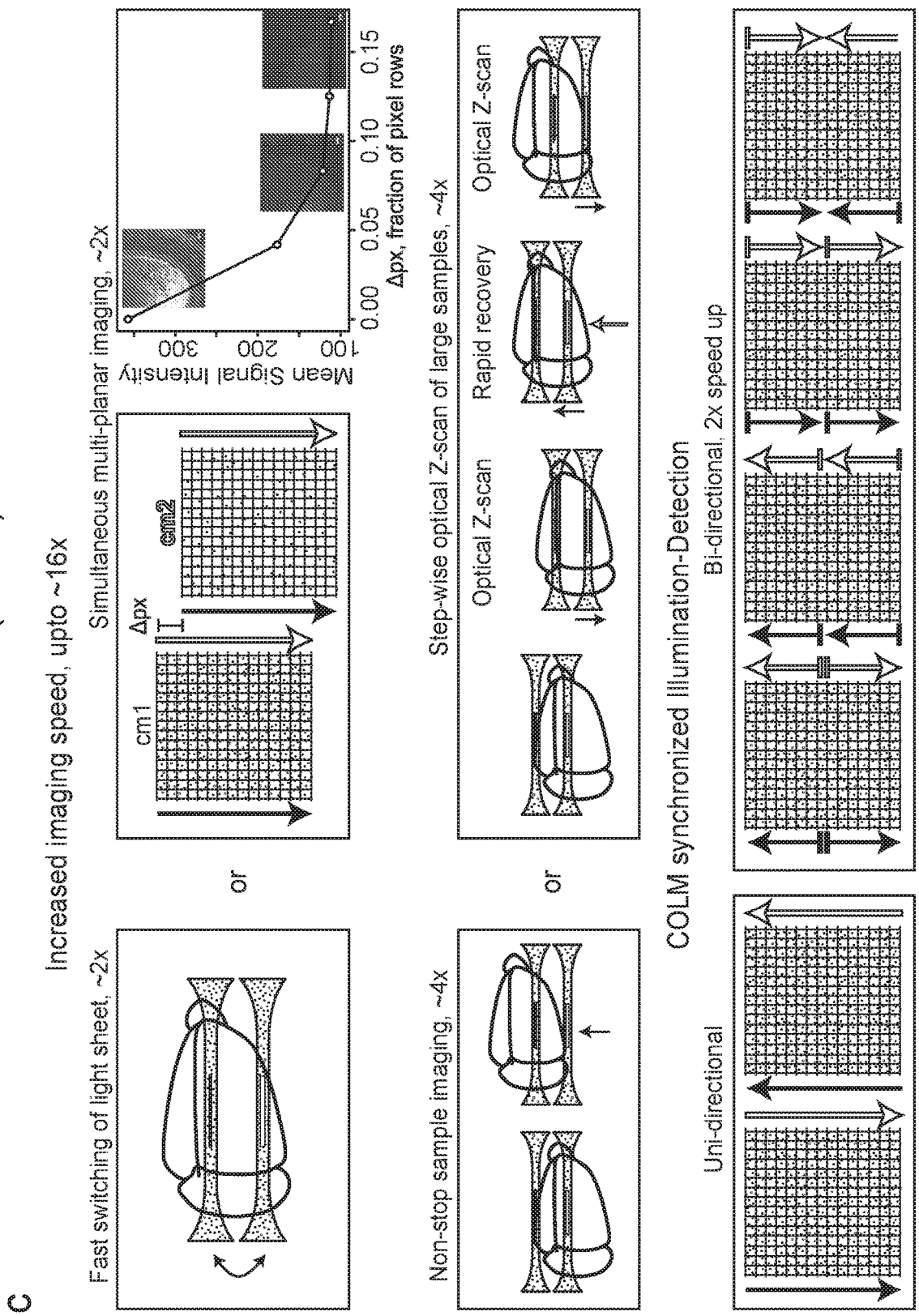

Referring now to FIG. 8, Panel a, an embodiment of a multi-planar COLM system is shown. As depicted, the system includes two illumination beam paths and two detection beam paths. The illumination beam paths are configured to illuminate a sample from opposite sides, and the detection beam paths are configured to image the sample from opposite sides. Simultaneous imaging of multiple planes is achieved by operating the two detection arms slightly shifted (about 100 microns is sufficient as shown in FIG. 8, Panel c.) from each other in the row-by-row readout direction.

Figure 9:
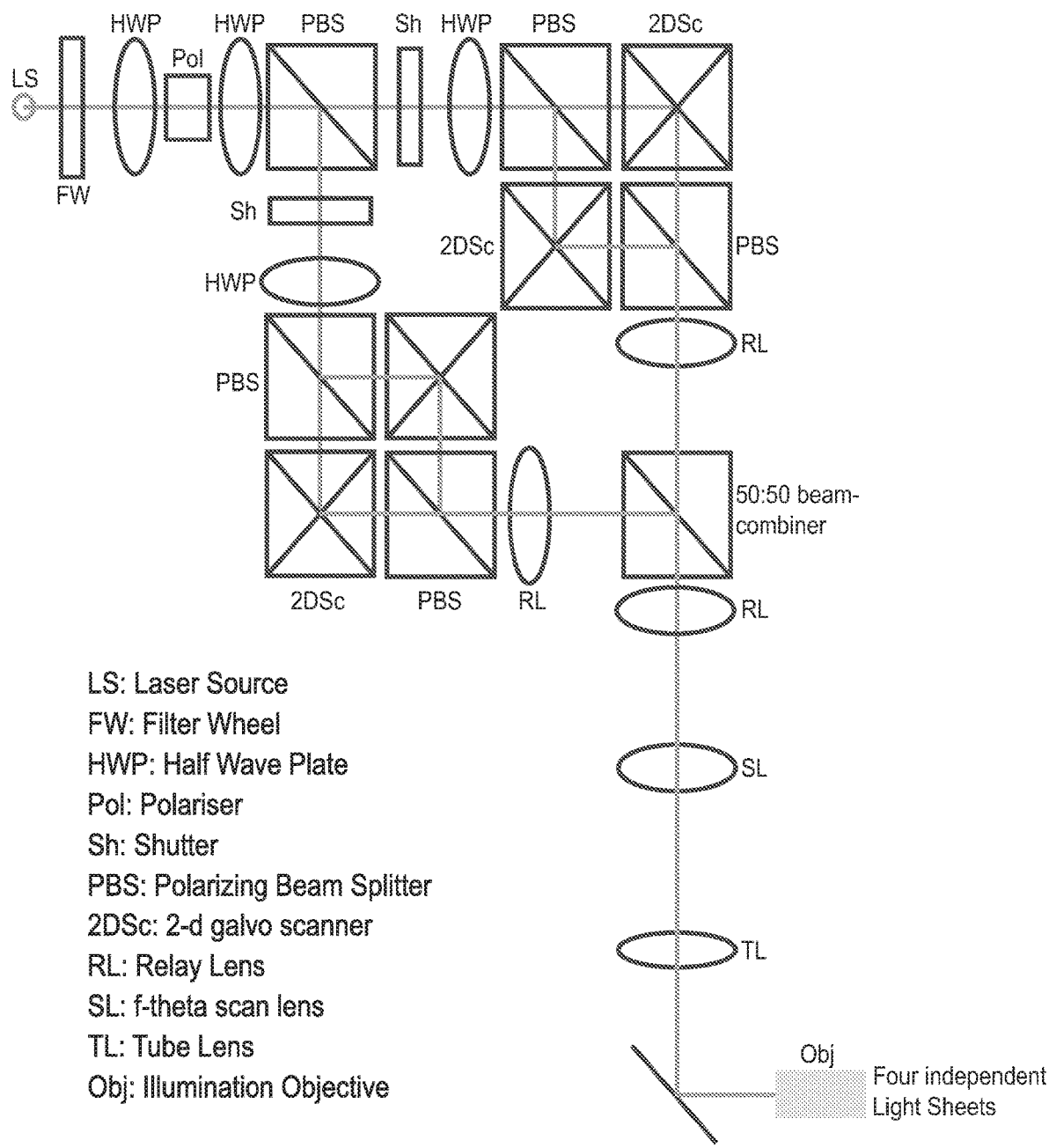
FIG. 9 shows a schematic representation of a multi-planar COLM system that can be used to generate four independent light sheets from one illumination beam path, thus creating eight independent light sheets in total in an embodiment that includes two illumination beam paths and two simultaneous imaging paths.

Referring now to FIG. 9, an embodiment of an illumination beam path of a multi-planar COLM system is shown. As depicted, the illumination beam path includes a variety of components that are configured to generate multiple independent light sheets. Specifically, the depicted embodiment is configured to generate four independent light sheets. It should be noted that one of ordinary skill in the art could also select various components in order to generate a different number of independent light sheets for use in the subject methods, described further herein.

Figure 11:
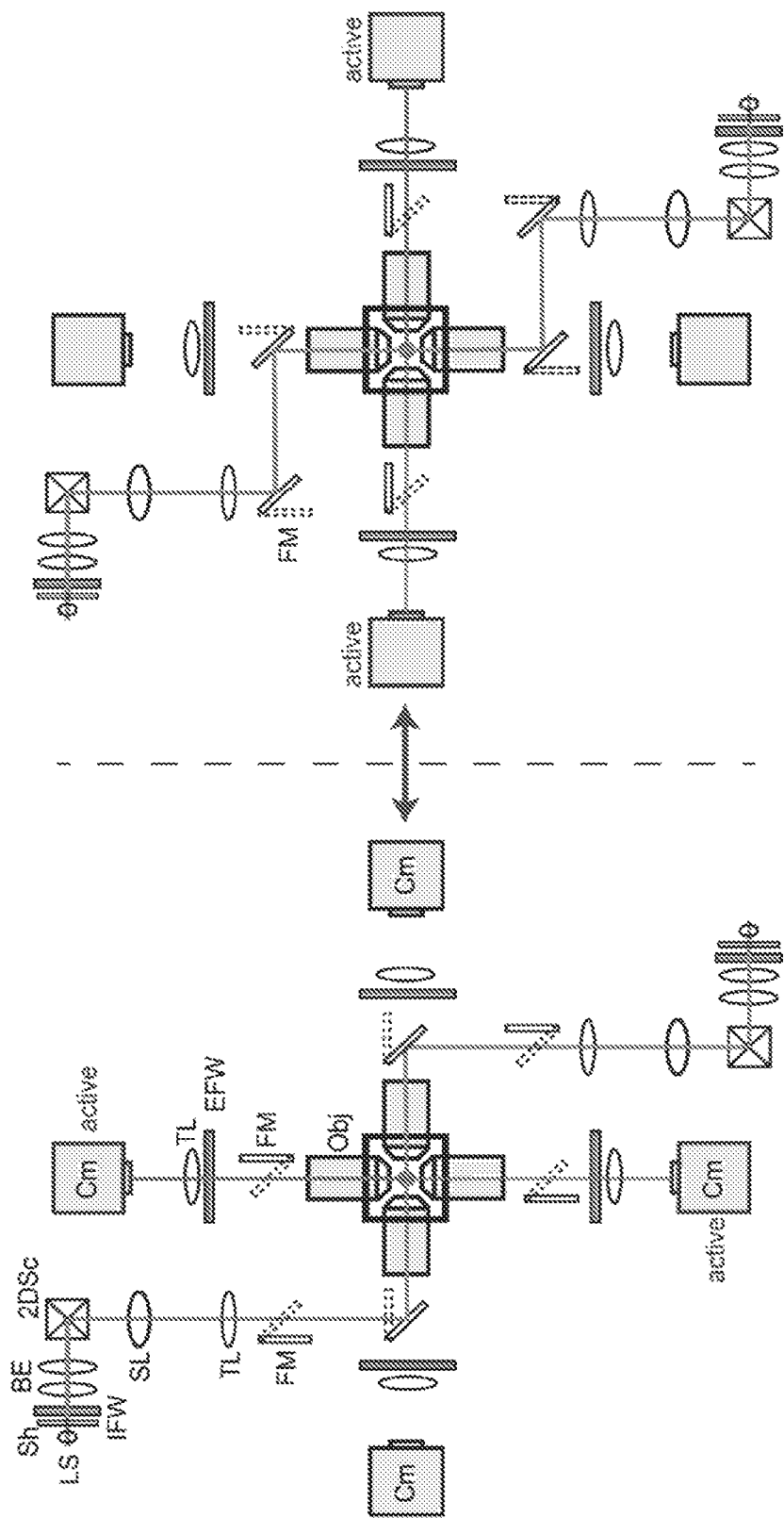
FIG. 11 shows a schematic representation of extended multi-planar COLM system with four detection beams paths, by employing motorized flip mirrors (FM). Using FM, a sample can be imaged from orthogonal views, which are then fused to generate isotropic resolution 3D volume data (LS: Laser Source; Sh: Shutter; IFW: Illumination Filter Wheel; BE: Beam Expander; 2DSc: 2D Galvo Scanner; SL: f-theta Scan Lens; TL: Tube Lens; FM: Motorized Flip Mirror; Obj: Illumination Objective; EFW: Emission Filter Wheel: and Cm: sCMOS or CCD Camera.

Referring now to FIG. 11, a two detection path can be extended to four detection paths by employing the use of motorized flip mirrors to redirect illumination beams to two different configurations that allow imaging by the corresponding pair of detection arms.

Methods

Aspects of the invention include methods that may be used for imaging large intact tissue samples. In some embodiments, the subject methods involve placing a sample in the sample chamber of an optically homogenous sample manipulation component, performing a calibration procedure to align a light sheet and a detection focal plane of a microscope device at a plurality of locations within the sample to acquire an alignment parameter for each location, performing an imaging procedure to collect an image from each of the plurality of locations within the sample, and constructing a three-dimensional image of the sample using the image from each location. Aspects of the methods are now further described in greater detail below.

As described above, aspects of the methods involve placing a sample in an optically homogenous sample manipulation component. In some embodiments, a sample is placed on a sample mount stage, such as an xyz-theta sample mount stage that is configured to move the sample in any direction. In some embodiments, the methods involve placing a sample in the sample chamber of an optically homogenous sample manipulation component, and filling the sample chamber with a solution that has a refractive index (RI) that matches that of the sample. In some embodiments, prior to performing the imaging analysis described herein, a sample may be prepared for microscopic analysis. In some embodiments, a sample is prepared by fixing the sample with a plurality of hydrogel subunits, polymerizing the hydrogel subunits to form a hydrogel-embedded sample, and clearing the hydrogel-embedded sample. Preparation methods are further described in International Patent Application No. PCT/US2013/031066, the disclosure of which is herein incorporated by reference in its entirety.

Aspects of the methods involve executing a calibration procedure that is used to align a detection focal plane of the microscope device with an illumination plane of the sample that is illuminated with a sheet of light. In some embodiments, the calibration procedure involves specifying a start position and an end position for the sample in the z-direction. In certain embodiments, the calibration procedure involves specifying a z-step value that is used to divide the sample into a plurality of planes in the z-direction, where each plane represents a two-dimensional segment or portion of the sample. In some embodiments, the z-step value ranges from 0.1 μm to 1 mm, such as 1 to 5 μm.

In some embodiments, the calibration procedure involves digitally dividing a sample into a plurality of tiles. By "tile" is meant an image of a discrete portion of a sample. When the field of view of a microscope objective is smaller than the sample itself, it may be necessary to collect multiple stacks of images in tiling arrangements, and then stitch together the tiles to generate a complete image. In some embodiments, the methods involve defining the coordinates of the two opposite corners of a region that will define the number of tiles, and setting a desired z-step value that will be used to collect a stack of tile images. In some embodiments, regions are selected as tiles having an overlap with each other ranging from 10 to 50%, such as 15 to 20%.

Aspects of the calibration procedure involve acquiring an alignment parameter for each of a plurality of locations within the sample. To acquire the alignment parameter at each location, a light sheet produced by moving a beam of light in one dimension is used to illuminate a plane of the sample. The plane of the sample that is illuminated by the light sheet is referred to herein as a "sample illumination plane" or "illumination plane." Alignment between the detection focal plane of the microscope and the sample illumination plane is accomplished by finding a maximum image quality measurement in a specified neighborhood corresponding to optimal alignment between the sample illumination plane and the detection focal plane. In some embodiments, the image quality measurement is an optical focus quality measurement that comprises a ratio of high frequency and low frequency signals in Fourier space.

The result of the calibration procedure is a plurality of alignment parameters that correspond to different locations within the sample. By applying an alignment parameter at a given location within the sample, optimal alignment between the detection focal plane of the microscope device and the light sheet is achieved at the location. In some embodiments, a z-step value of 1 mm is used to carry out the calibration procedure, and linear interpolation between two adjacent locations within the sample is used to determine an alignment parameter at a location between the two adjacent locations. In this way, the calibration procedure can be performed using a z-step value of 1 mm, and the results can then be applied to the entire sample to determine an alignment parameter at any location. In some embodiments, the calibration procedure is automated. In some embodiments, a processor executes instructions that cause a controller to execute the calibration procedure and acquire a plurality of alignment parameters for the sample.

As described above, aspects of the methods include performing an imaging procedure that utilizes the alignment parameters to align a detection focal plane of the microscope device with an illumination plane of the sample. In some embodiments, the imaging procedure involves aligning a detection focal plane of the microscope device with an illumination plane of the sample, illuminating a linear portion of the illumination plane with a beam of light from a light source, and capturing a plurality of emitted light signals from the illuminated linear portion of the illumination plane with the camera. In certain embodiments, alignment of a detection focal plane of the microscope device and an illumination plane of the sample is synchronized, such that illumination of the illumination plane is carried out at the same time that the detection focal plane is aligned with the illumination plane. In this way, only the portion of the sample that is actively being imaged is illuminated, thereby reducing photo-bleaching of signals in the sample that may result from excessive illumination.

In some embodiments, the imaging procedure involves directing a beam of light from a light source to sweep across an illumination plane and thereby illuminate a plurality of linear portions of the illumination plane. In some embodiments, as the beam of light sweeps across the illumination plane, a plurality of emitted light signals from each different linear portion of the illumination plane is captured by the camera, resulting in a two dimensional image of the sample that coincides with the illumination plane. In some embodiments, the period of time during which an illumination plane of the sample is illuminated ranges from 1 millisecond (ms) to 1 second, such as 5 to 100 ms.

In some embodiments, the methods involve directing multiple independent light sheets to illuminate different portions of a sample. For example, in some embodiments, two or more light sheets are used to illuminate a sample from opposite sides of the sample. In some embodiments, a plurality of light sheets are used to illuminate the sample, such as two or more, three or more, four or more, five or more, six or more, seven or more, or up to eight or more light sheets. In some embodiments, a single light sheet is used to illuminate two or more different portions of a sample by quickly moving, or "switching" the light sheet from one position to another.

In some embodiments, the imaging procedure further involves moving the sample in the z-direction such that the light sheet will illuminate a new illumination plane, and repeating the imaging procedure to generate another two dimensional image of the sample coinciding with the new illumination plane. In some embodiments, the sample remains stationary while the light sheet and the detection objective are moved to image a new illumination plane. In some embodiments, the imaging procedure involves synchronously moving the optics (e.g., the objectives in the illumination beam path(s)) and the light sheets that are used to illuminate the sample. In some embodiments, the imaging procedure involves continuously moving the sample with the sample manipulation components at a defined rate, such that the camera in the detection beam path can continuously image various planes of the sample as they are illuminated. Any of the above-described methodology can be implemented with respect any given light sheet. As such, utilizing multiple light sheets in a COLM system can be used to increase the overall speed of the imaging procedure for a particular sample, as well as increase the size of a sample that can be imaged using the subject systems and methods.

In some embodiments, the result of the illumination procedure is a plurality of two dimensional images of the sample, each corresponding to a different illumination plane of the sample. In some embodiments, the imaging procedure is automated. In some embodiments, a processor executes instructions that cause a controller to execute the imaging procedure and acquire a plurality of two dimensional images of the sample, each corresponding to a different illumination plane of the sample.

In some embodiments, the imaging procedure further involves data processing of a plurality of two dimensional images to form a three dimensional image of the sample. In some embodiments, two or more different two dimensional images of a sample may be combined, or "stitched" together to form a single two dimensional image of a plane of the sample. For example, as described above, when a sample is imaged using two or more different independent light sheets, the images obtained from each light sheet may be combined to form a single two dimensional image corresponding to a given plane of the sample.

Three dimensional reconstruction software is commercially available, and can be used to stitch together tiled images and/or reconstruct a plurality of two dimensional images into a three dimensional image. Commercially available software programs include those from Imaris, Bitplane and Amira, as well as open source software such as the stitching plugins in Fiji, XuvTools, Vaa3D plugin, and TeraStitcher. In some embodiments, manual or semi-automatic tracing of neuronal morphology in a sample comprising neuronal tissue can be performed using specific modules in commercial software, such as Imaris and Amira, or with open-source tools such as Neuromantic.

Figure 7:
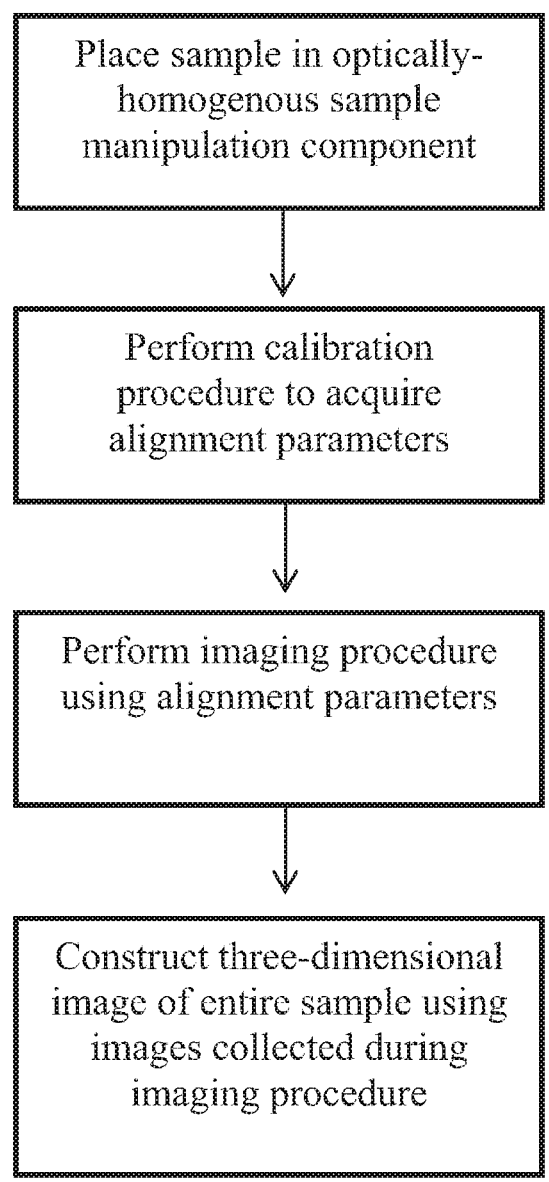
FIG. 7 shows a block flow diagram of one embodiment of the methods.

Referring now to FIG. 7, a block flow diagram of one embodiment of the methods is shown. In the depicted embodiment, the method includes placing a sample in the optically-homogenous sample manipulation component, performing a calibration procedure on the sample to acquire a plurality of alignment parameters, performing an imaging procedure on the sample using the alignment parameters, and constructing a three-dimensional image of the entire sample using the images captured during the imaging procedure.

Referring now to FIG. 8, Panel b, an embodiment of a method for obtaining high-quality deep images or a large intact sample is shown. As depicted, two independent planes, illuminated with two aligned sheets of light (either one beam from each side illuminating the two different planes, or two from each side, with one from each plane side illuminating the same plane and the remaining illuminating the other plane), are imaged, either simultaneously or sequentially from opposite detection arms. A two dimensional image of the sample is generated from each light sheet. Panel b demonstrates images of the same plane imaged from two opposite detection arm. The detection arms can be aligned precisely (for example, with sub-microns accuracy). Panel b demonstrates images from slightly misaligned arms, and that by small corrections in the X or Y direction can be superimposed. Using this method, larger samples can be imaged, as the overall working distance of the combination of both objectives is increased by two fold through the addition of the second objective in the second detection beam path.

Referring now to FIG. 8, Panel c, various methods of increasing imaging speed are shown. As depicted, fast switching of a light sheet may to illuminate two independent planes be used to increase overall imaging speed. Similarly, simultaneous multi-planar imaging can also be used to increase the overall speed of the imaging process. Non-stop sample imaging, wherein multiple light sheets are continuously moved through the sample or the sample is moved continuously through multiple light sheets while continuously acquiring images, can also be used to increase the overall speed of the imaging process. In addition, step-wise optical z-scanning can be used with multiple light sheets to sequentially image different optical planes of a sample. Uni-directional and bi-directional synchronized illumination and detection can also be used to increase the overall speed of the imaging process. In bi-directional synchronized illumination and detection, two or more independent light sheets are used to illuminate and image different portions of a sample, as depicted in FIG. 8, Panel c. The use of multiple light sheets moving in different directions increases the overall speed of the imaging process.

Referring now to FIG. 11, a method of increasing axial (z-resolution) is shown. By imaging a sample from four independent, orthogonally arranged, signal detection arms, a 3D image is acquired from four orthogonal views. By fusing these four views, improvement in axial resolution (z-resolution) is achieved. FIG. 11 shows two automatically switchable configurations wherein a sample is first image by a set of two detection arms, and then by an orthogonally arranged part of the detection arm. This switching is performed using fast, precise flip mirrors, which either reflect excitation light or allow it to pass through unhindered.

Applications

Using the subject methods and systems, the ordinarily skilled artisan will be able to image any biological tissue. Methods and systems may be used to image a specimen from any plant or animal, e.g. vertebrate or invertebrate, e.g. insect, worm, xenopus, zebrafish, mammal, e.g. equine, bovine, ovine, canine, feline, murine, rodent, non-human primate or human. The specimen may be of any tissue type, e.g. hematopoietic, neural (central or peripheral), glial, mesenchymal, cutaneous, mucosal, stromal, muscle (skeletal, cardiac, or smooth), spleen, reticulo-endothelial, epithelial, endothelial, hepatic, kidney, pancreatic, gastrointestinal, pulmonary, fibroblast, and other cell types. In some instances, the specimen is the organism, e.g. a worm, an insect, a zebrafish, or a developing embryo. In other instances, the specimen is a whole organ, e.g. the whole brain of a rodent. In other instances, the specimen is a portion of an organ, i.e. a biopsy, e.g. a biopsy of a transplanted tissue. The specimen may be freshly isolated or preserved, e.g. snap frozen. The specimen may have "normal" pathology, or may display signs of abnormal or disease-associated pathology. Examples of such specimens include those obtained from tumors or tumor-associated tissues, diseased tissues, and the like. As such, the subject methods and systems find use in pathological analysis of tissue specimens.

The subject methods and systems find use in conjunction with techniques for preparing biological specimens for microscopic analysis. In some embodiments, the methods involve preparing a sample for the subject imaging analysis by fixing the sample with a plurality of hydrogel subunits, polymerizing the hydrogel subunits to form a hydrogel-embedded sample, and clearing the hydrogel-embedded sample. Further details regarding the preparation of specimens for microscopic analysis can be found in International Patent Application No. PCT/US2013/031066, the disclosure of which is herein incorporated by reference in its entirety. As used herein, the term "CLARITY" refers to a method of preparing a biological specimen for analysis as disclosed in PCT/US2013/031066.

The subject methods and systems find many uses. For example, the subject methods may be applied to the study of the connectivity of the central nervous system. "Connectivity" as used herein generally means the connections between neurons, and includes connections at the single cell level, e.g. synapses, axon termini, dendritic spines, etc. and connections between groups of neurons and regions of the CNS as major axon tracts, e.g. corpus callosum (CC), anterior commissure (AC) hippocampal commissure (HC), pyramidal decussation, pyramidal tracts, external capsule, internal capsule (IC), cerebral peduncle (CP), etc. A whole brain and/or spinal cord specimen or region thereof (e.g. cerebrum (i.e. cerebral cortex), cerebellum (i.e. cerebellar cortex), ventral region of the forebrain (e.g. striatum, caudate, putamen, globus pallidus, nucleus accumbens; septal nuclei, subthalamic nucleus); regions and nuclei of the thalamus and hypothalamus; regions and nuclei of the deep cerebellum (e.g., dentate nucleus, globose nucleus, emboliform nucleus, fastigial nucleus) and brainstem (e.g. substantia nigra, red nucleus, pons, olivary nuclei, cranial nerve nuclei); and regions of the spine (e.g. anterior horn, lateral horn, posterior horn)) may be prepared post-mortem and the connectivity of the neurons therein microscopically analyzed using the subject methods and systems, e.g. obtained, stored, rendered, used, and actuated, e.g. to provide the full connectivity of a brain, e.g. a human brain, after death. Such studies will contribute greatly to the understanding of how the brain develops and functions in health and during disease, and of the underpinnings of cognition and personality.

As another example, the subject methods and systems may be employed to diagnose or monitor disease. "Diagnosis" as used herein generally includes a prediction of a subject's susceptibility to a disease or disorder, determination as to whether a subject is presently affected by a disease or disorder, prognosis of a subject affected by a disease or disorder (e.g., identification of cancerous states, stages of cancer, likelihood that a patient will die from the cancer), prediction of a subject's responsiveness to treatment for the disease or disorder (e.g., positive response, a negative response, no response at all to, e.g., allogeneic hematopoietic stem cell transplantation, chemotherapy, radiation therapy, antibody therapy, small molecule compound therapy) and use of therametrics (e.g., monitoring a subject's condition to provide information as to the effect or efficacy of therapy). For example, a biopsy may be prepared from a cancerous tissue and microscopically analyzed using the subject methods and systems to determine the type of cancer, the extent to which the cancer has developed, whether the cancer will be responsive to therapeutic intervention, etc. As another example, a biopsy may be prepared from a diseased tissue, e.g. kidney, pancreas, stomach, etc., and imaged using the subject methods and systems to determine the condition of the tissue, the extent to which the disease has developed, the likelihood that a treatment will be successful, etc. The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease. The terms "individual," "subject," "host," and "patient," are used interchangeably herein and refer to any mammalian subject for whom diagnosis, treatment, or therapy is desired, particularly humans.

Similarly, the subject methods and systems may be used to monitor tissue grafts to determine how well the subject has accepted a transplanted organ/tissue, e.g. heart, kidney, liver, or other organ. In such instances, a biopsy of the transplanted organ may be microscopically analyzed using the subject methods and systems to look for, e.g., tissue integrity, tissue vascularization, the infiltration of immune cells, etc.

The subject methods and systems also provide a useful system for screening candidate therapeutic agents for their effect on a tissue or a disease. For example, a subject, e.g. a mouse, rat, dog, primate, human, etc. may be contacted with a candidate agent, an organ or a biopsy thereof may be prepared, and the prepared specimen microscopically analyzed using the subject methods and systems to look for one or more cellular or tissue parameters. Parameters are quantifiable components of cells or tissues, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values. Thus, for example, one such method may comprise detecting cellular viability, tissue vascularization, the presence of immune cell infiltrates, efficacy in altering the progression of the disease, etc. In some embodiments, the screen includes comparing the analyzed parameter(s) to those from a control, or reference, sample, e.g. a specimen similarly prepared from a subject not contacted with the candidate agent. Candidate agents of interest for screening include known and unknown compounds that encompass numerous chemical classes, primarily organic molecules, which may include organometallic molecules, inorganic molecules, genetic sequences, etc. Candidate agents of interest for screening also include nucleic acids, for example, nucleic acids that encode siRNA, shRNA, antisense molecules, or miRNA, or nucleic acids that encode polypeptides. An important aspect of the invention is to evaluate candidate drugs, including toxicity testing, and the like.

The subject methods and systems may also be used to visualize the distribution of genetically encoded markers in whole tissue at subcellular resolution, for example, chromosomal abnormalities (inversions, duplications, translocations, etc.), loss of genetic heterozygosity, the presence of gene alleles indicative of a predisposition towards disease or good health, likelihood of responsiveness to therapy, ancestry, and the like. Such detection may be used in, for example, diagnosing and monitoring disease as, e.g., described above, in personalized medicine, and in studying paternity.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, dimensions, etc.) but some experimental errors and deviations should be accounted for.

Overview of Examples

Figure 2:
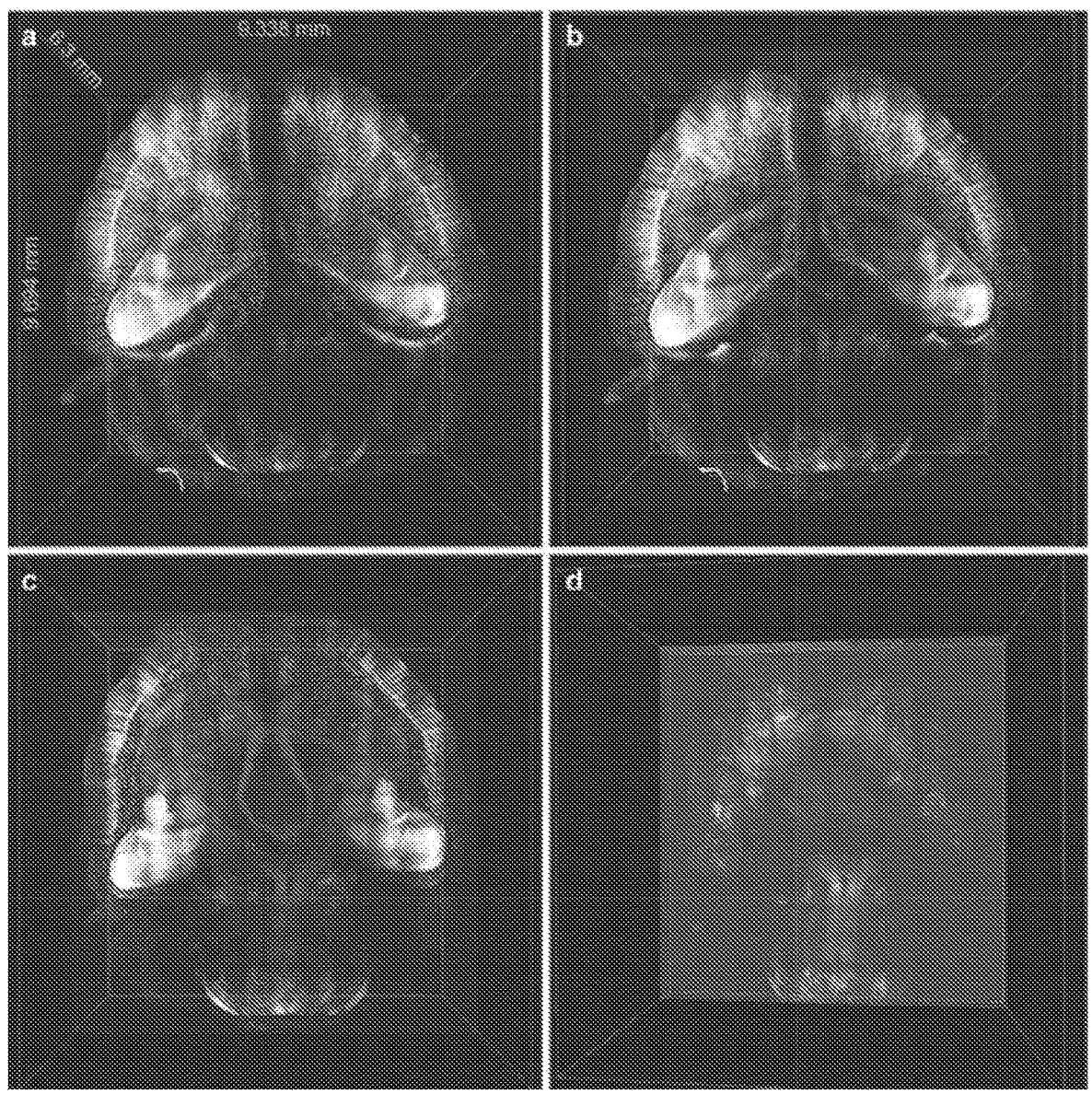
FIG. 2, Panels a-d show rendered images of the internal details of an intact mouse brain volume acquired from an intact clarified Thy1-eYFP mouse brain using COLM.
Figure 3:
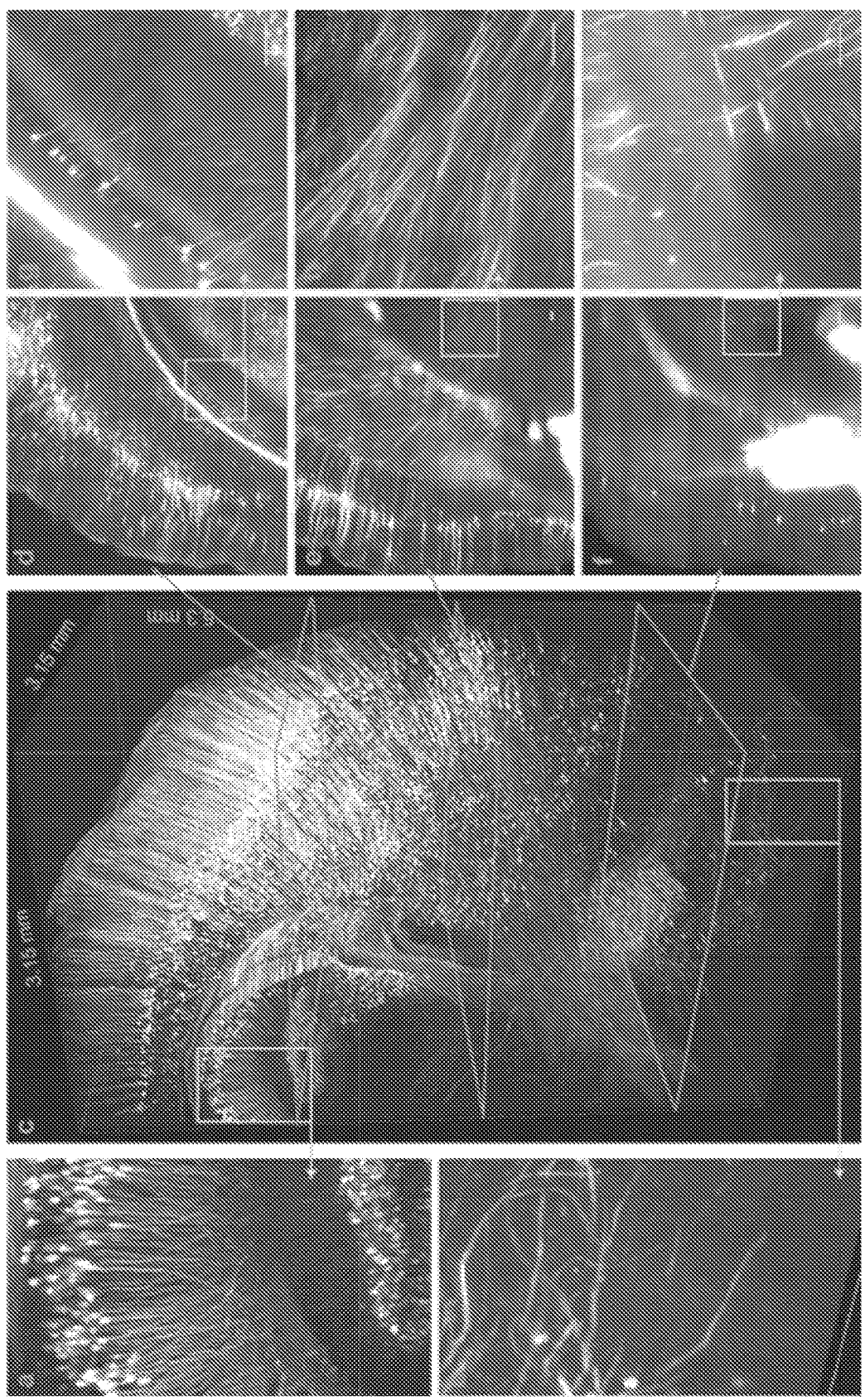
FIG. 3, Panels a-i provide various magnified views of a large brain volume. Panels d-i show high resolution images over a 50 micron-thick volume acquired from an intact clarified Thy1-eYFP mouse brain using COLM. All scale bars: 100 µm.
Figure 4B:
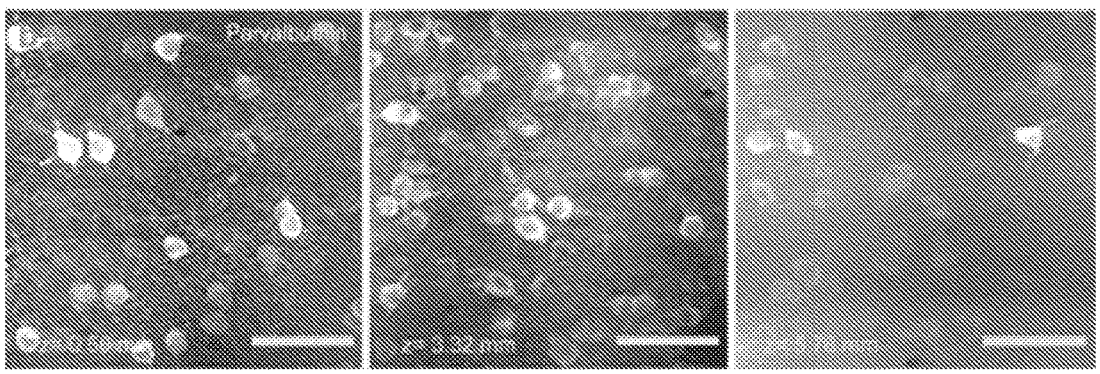
Figure 5:
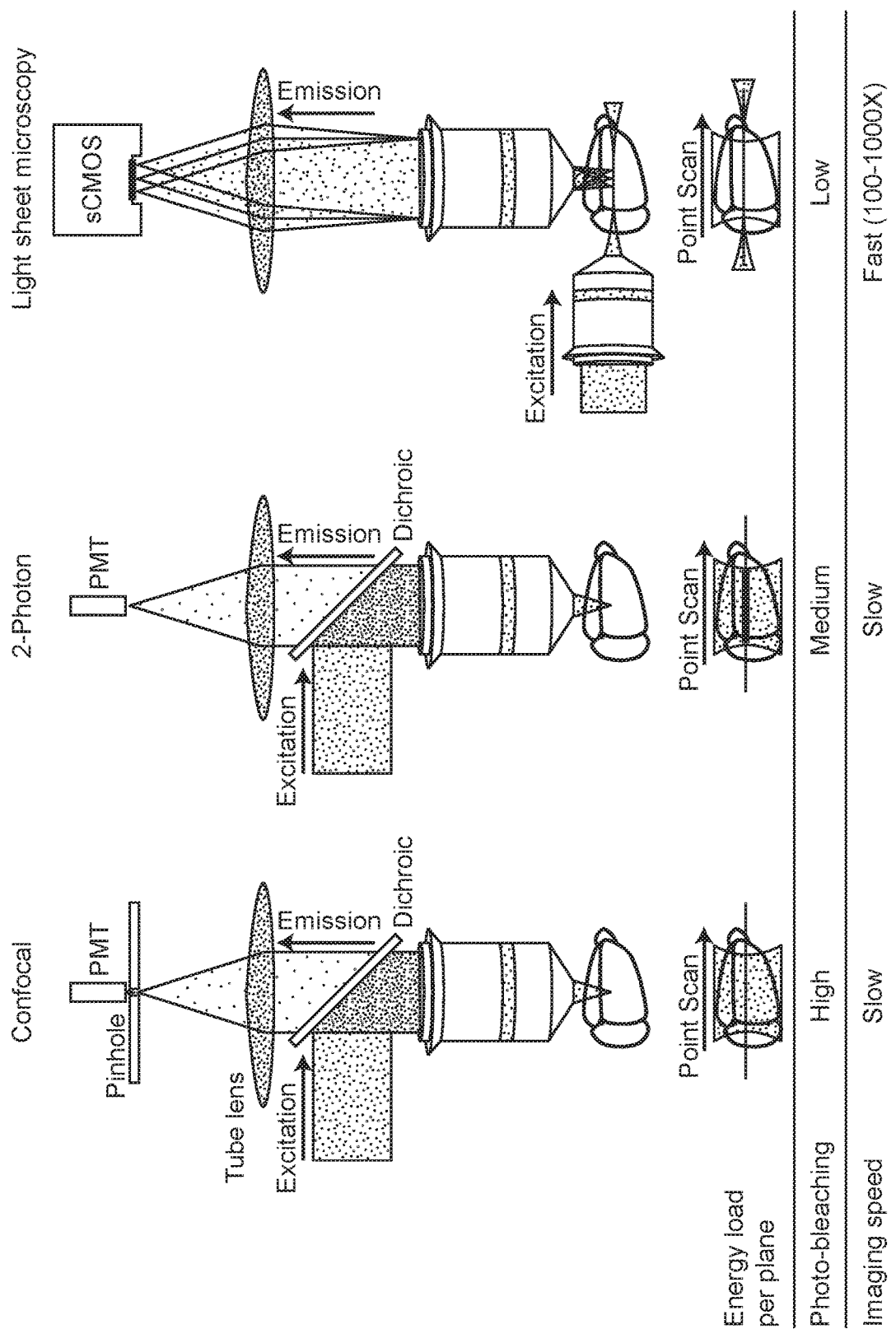
FIG. 5 shows a schematic comparison of confocal, two-photon and light sheet microscopy.
Figure 10:
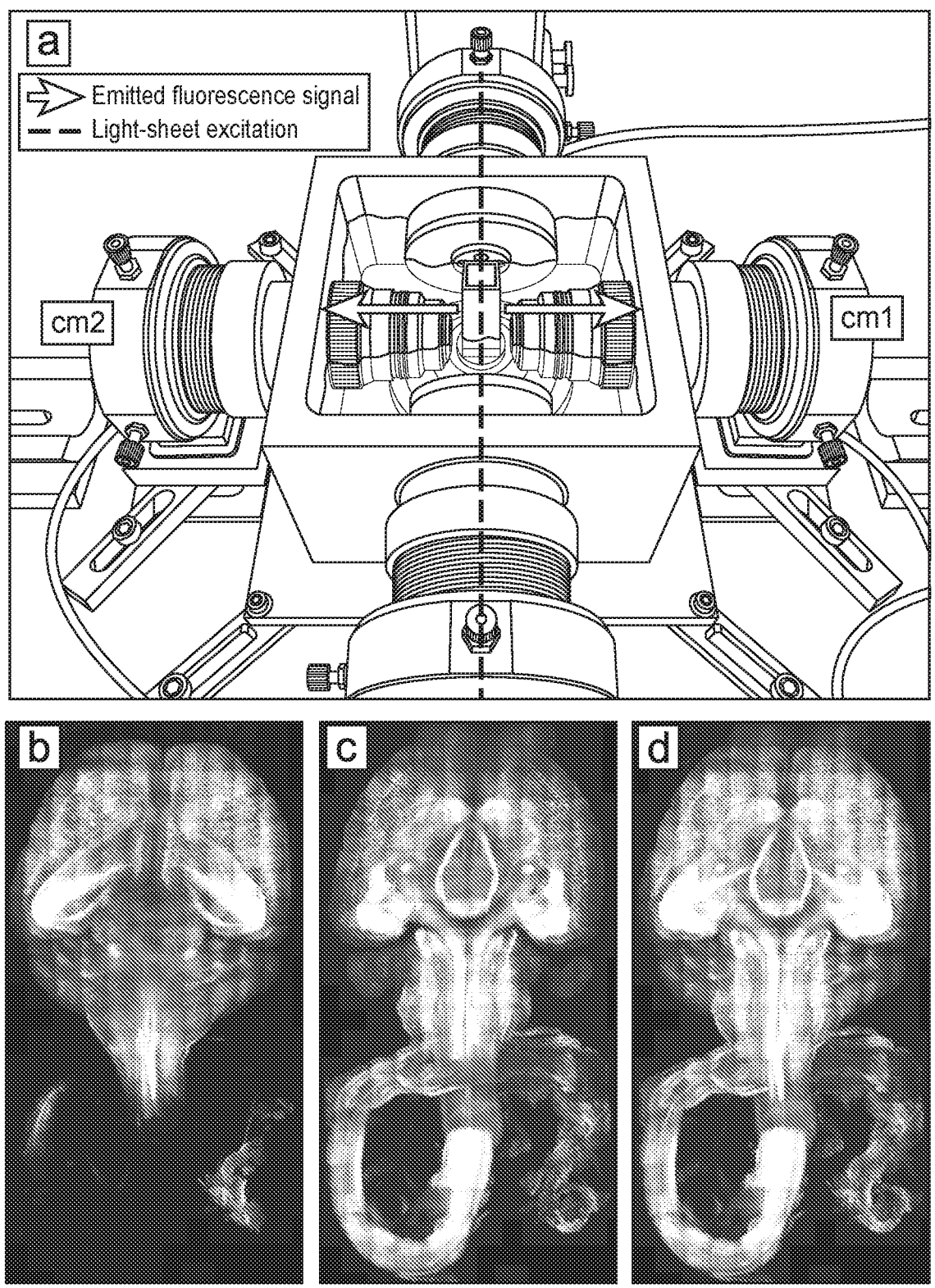
FIG. 10, Panel a shows a picture of the physical implementation of multi-planar COLM system detailed in FIG. 8-Panel a. Panel b, c and d present an example dataset of entire central nervous system (Brain and Spinal Cord) of adult mouse, acquired using two detection system. Panel b is maximum projection of 3D Image from one camera, Panel c from other, and d after merging the two.

As provided above, in light sheet microscopy a sample is illuminated from the side with a thin sheet of light, and the emitted light signal (e.g., fluorescence signal) is detected with an in-focus orthogonally arranged objective. The optical sectioning is achieved by the confinement of illumination to a selective plane, which allows use of fast CCD or sCMOS cameras to capture the whole image simultaneously, and results in an increase in imaging speed. Moreover, light sheet microscopy minimizes photo-bleaching (FIG. 5) by confining illumination to the plane of interest. These properties of light sheet microscopy are well-suited for the imaging of large clarified samples, produced, for example, by the CLARITY process. CLARITY optimized light-sheet microscopy (COLM) (FIG. 1A-D) allows the entire depth of a clarified sample, e.g., a mouse brain (>5 mm), to be imaged at high resolution using CLARITY-optimized objectives (FIGS. 2, 3, 4B), and high-speed collection of large clarified volumes leads to vastly decreased photo-bleaching (FIGS. 2, 3). Two detection arms allow increased imaging quality over larger depth as a part of the sample is imaged from the detection arm nearest to it. (FIG. 10 Panels b, c and d.)

Materials and Methods

Reagents and Samples

Hydrogel monomer (HM) solution 400 ml HM solution was prepared by mixing 40 mL of 40% acrylamide (Bio-Rad, cat. no. 161-0140, 4% final concentration), 10 mL of 2% bisacrylamide (Bio-Rad, cat. no. 161-0142; 0.05% final concentration), 40 mL of 10× PBS, 100 mL of 16% PFA (Electron Microscopy Sciences, cat. no. 15710-S; 4% final concentration), 210 mL of distilled water and 1 g of VA-044 thermal initiator (Wako, cat. no. VA-044; 0.25% w/v final concentration). All the reagents were kept on ice. 40 mL of the HM solution were aliquoted into 50 mL Falcon tubes and stored at −20° C. until needed. Acrylamide and bisacrylamide concentration in HM solution can be proportionally reduced to speed up the clearing process. Concentrations of 0.5%/0.0125% acrylamide/bisacrylamide ranging up to 4.0%/0.05% were successfully employed; however lower acrylamide/bisacrylamide concentrations may be employed to start with as clearing speed is increased several-fold.

SDS/borate clearing buffer (SBC) Stocks of 20% SDS (Sigma cat no. L337 or Amresco cat no. 0837; in $H_2O$) and 1 M boric acid buffer (pH adjusted to 8.5) were prepared. Final clearing buffer was freshly prepared by diluting 20% SDS and 1 M boric acid buffer 5-fold in distilled water.

Other reagents Other reagents used were as follows: FocusClear (CelExplorer Labs); Custom Refractive Index liquids (RI 1.454, cat. no. 1806Y, Cargille Labs); Clearing solution (Boric Acid (Sigma, cat. no. B7901); Sodium Hydroxide pellets (EMD, cat. no. SX0590-3).

Imaging samples Imaging samples were prepared from adult Thy1-eYFP or WT mice. All animal experiments were carried out with Stanford University Institutional review panel approval.

Molecular Labeling

A tissue sample may have endogenous transgenic expression of fluorophores to label molecular and structural details in the sample, but additionally, immunohistochemistry can be used for labeling structure and molecules of interest.

Tissues were washed thoroughly in PBST (or boric acid buffer/0.1% Triton X-100 wash for whole brains) for at least 1 day at 37° C. Samples were incubated in primary antibody/PBST solution (beginning with 1:50 dilution) for 2 days at 37° C. for tissue blocks, or for up to a week for the whole intact brain. ~1M borate/0.1% Triton X-100 buffer (pH 8.5) can also be used in place of PBST for antibody incubations to reduce background staining Antibodies were incubated with a 1 mm-thick block in 1 mL solution or with a whole mouse brain in 5 mL solution with scaled-up antibody volumes supplemented periodically; for example, 50 μL anti-TH Ab (10-20 μl) can be added, followed by 20 μL more every two days for ~1 week. High antibody concentrations (1:20-1:100) were required for effective immunostaining to ensure deep penetration into tissue and to overcome the large aggregate number of antibody binding sites over the volume.

A second major factor for successful immunostaining was complete removal of lipids during clearing.

Primary antibodies were washed off with PBST buffer at 37° C. for 1 day for tissue blocks and for 2-3 days for whole brain (refresh buffer every 4-6 hours). Samples were incubated with desired secondary antibody (1:50-1:100) in PBST at 37° C. for 2 days for tissue blocks or for up to 1 week for whole brain. Note that a nuclear labeling dye, such as DAPI, can also be added at this step. Secondary antibodies were washed off with PBST at 37° C. for 1 day for tissue blocks and 2-3 days for whole brain. To prepare for imaging, the tissue was transferred into FocusClear for refractive index homogenization. Multiple rounds of labeling were performed by eluting (removing) the prior label after imaging by incubating the tissue in clearing buffer at 60° C. overnight, followed by another round of labeling.

Equipment Setup

CLARITY Optimized Light-Sheet Microscope

A light sheet microscope consists of one or more standard wide field detection optical arms, which include a detection objective, a tube lens and a camera, and one or more orthogonally-arranged independent illumination arms consisting of a low NA objective, tube lens and either a cylindrical lens to generate a static light sheet or galvanometer-scanners/f-theta lens for creating dynamic light sheets with a Gaussian or Bessel beams.

CLARITY optimized light-sheet microscopy (COLM) was developed to maximize compatibility of clarified samples with light sheet microscopy, using CLARITY objectives (25× and 10×, Olympus), a fast sCMOS camera, two-axis galvo scanners along with the f-theta lens, a low NA objective to generate dynamic light sheets using a Gaussian beam, an optimized sample chamber (detailed in the following section) and an xyz-theta sample mount stage that provided a long travel range of 45 mm in each of the dimensions to allow imaging of large samples (FIGS. 1A-D).

COLM employed synchronized illumination-detection to improve imaging quality, especially at higher depths (FIG. 1C), exploiting the uni-directional readout (as opposed to standard bi-directional) mode available in the next generation sCMOS cameras. The scanning beam (which created the dynamic light sheet) was synchronized with the uni-directional single line readout of the emitted signal, resulting in a virtual confocal-slit arrangement, which rejected out-of-focal-plane signal due to scattering deeper in the sample. Automated-alignment parameter calibration (using linear adaptation) in COLM corrected for misalignment artifacts across the whole sample space (FIG. 1D). The control electronics design and parts for COLM are summarized in FIG. 6. FPGA logic was used to control and synchronize various parts of the microscope.

Sample Mounting Apparatus for COLM

A component of COLM was a CLARITY optimized sample mounting strategy that minimizes optical inhomogeneity along one or more detection paths (FIG. 1B). Clarified whole mouse brain (or any large clarified intact tissue such as a spinal cord) was mounted in a cuvette made of fused quartz glass (standard cuvettes used for spectrophotometer measurements) filled with FocusClear; the refractive index of fused quartz (~1.458) was nearly identical to that of FocusClear. Using a bottom-adapter (FIG. 1B), the sample cuvette was mounted onto the xyz-theta stage, inside the sample chamber (FIG. 1B). The much larger chamber was then filled with a relatively economically-priced custom refractive index matching liquid (RI 1.454, cat. no. 1806Y, Cargille Labs), resulting in an optically homogeneous sample manipulation system. RI liquid cost several hundred dollars per half liter, which was enough to fill the sample chamber (and more than an order of magnitude cheaper than FocusClear) and could be re-used many times. Alternatively, the chamber also could be filled with 87% glycerol.

Computational Workstation for Data Analysis

Since the image data sizes are very large, it was important to employ a computational workstation with abundant RAM, multicore CPUs and an excellent graphics card. Data shown here were handled on a workstation with the following configuration: Intel server board S2600CO, two Intel Xeon E5-2687W 8C CPUs, ~130 GB of DIMM RAM, ~8 TB of hard disk (Seagate Savvio 10K), NVidia K5000 graphics card and a high-resolution monitor (NEC MultiSync PA301W 30 inch 2560×1600).

Imaging and Analysis

CLARITY Optimized Light-Sheet Microscopy

The sample (e.g. intact mouse brain) was mounted in a quartz cuvette of appropriate dimension, so that the sample remained stationary while imaging (FIG. 1B). Note that many different sizes of quartz cuvettes are available from vendors (such as Starna Cells); a small piece of acrylamide gel (or similar transparent material) may be used to provide structural padding on the side opposite to the imaging side. For adult mouse brain, 10×5 mm or 10×10 mm base cuvettes with padding may be used, depending on age.

The cuvette was filled with FocusClear, just enough to cover the entire sample. Using an adapter, the cuvette was mounted on the xyz-theta stage (FIG. 1B). Bubbles or dust particles were avoided as they interfere with the imaging.

Clarified samples, such as intact adult mouse brain, were mounted in a quartz cuvette filled with refractive index matching solution such as FocusClear. The refractive index of quartz glass (~1.458) was nearly identical to that of FocusClear (~1.454). A bottom-adapter was used to attach the cuvette to the xyz-theta stage in the sample chamber, which was then filled with a matching refractive index liquid (~1.454). This resulted in an optically homogenous sample manipulation system with minimal refractive-index transition boundaries.

Tiling parameters were set as follows. Some samples were larger than the field of view of the objective used, and therefore required tiling of image stacks to cover the entire sample. To specify the number of tiles, the coordinates of the two opposite corners of the region of interest were defined, with 20% or more tile overlap. The start and end z-position of the stack were specified by finding the first and last image frames containing useful signal from the sample, and then the desired z-step value was set.

Any misalignment between a light sheet and a detection focal plane, which (particularly during imaging of large samples) can result in blurred images, was adjusted. The light sheets and focal-plane alignment parameters were optimized over the entire sample space as defined above. This was achieved by optimizing these parameters at every millimeter of tissue for all the tiles, and then linearly interpolating the values for z-steps in between these millimeter steps. Optimal parameters were identified by finding maxima in a specified neighborhood corresponding to the image quality measure; to automate this process, an optical focus-quality measure was implemented, as the ratio of high frequency and low frequency signal in Fourier space.

The imaging experiment was initiated and data was collected as follows. Two light sheets were created from opposite sides and the emitted fluorescence was imaged with an in-focus detection objective, tube lens and sCMOS camera. Illumination and emission filter wheels (motorized) were used to generate well-defined excitation light and emission signal bands respectively.

Synchronized illumination and detection was achieved by synchronizing the scanning beam with the uni-directional readout of a sCMOS camera chip, resulting in a virtual-slit effect that allowed substantially improved imaging quality, as illustrated by the images shown acquired from the same plane with COLM and with conventional light-sheet microscopy (FIG. 1C). Signal intensity profile of a field in images acquired with COLM was improved compared to images acquired with conventional light-sheet microscopy (FIG. 1C, graph at right).

To adjust for refractive index inhomogeneity of large clarified samples, misalignment of illumination was corrected with the focal plane of the detection objective with a linear adaptive calibration procedure before starting the imaging experiment as described above.

3D Reconstruction and Analysis

Three-dimensional reconstructions were performed either with commercial software (e.g., Imaris from Bitplane or Amira) or via free/open-source projects (eg, Vaa3D, www.vaa3d.org). The stitching of tiles was performed with TeraStitcher. Manual or semi-automatic tracing of neuronal morphology can be performed using specific modules in commercial software such as Imaris and Amira, or with open-source tools such as Neuromantic.

Example 1

Ultrafast Imaging of Whole Mouse Brain Using COLM

Thy1-eYFP mouse brain was perfused with 0.5% acrylamide monomer solution, and clarified passively at 37° C. with gentle shaking Camera exposure time of 20 ms was used, and the refractive index liquid 1.454 was used as immersion media. The entire dataset was acquired in ~4 hours using a 10×, 0.6 NA objective. Internal details of the intact mouse brain volume were visualized by successive removal of occluding dorsal-side images (FIG. 2, Panels b, c and d). FIG. 10 Panels b,c and d present an example of imaging entire central nervous system (Brain and Spinal cord attached) using two independent detection arm COLM implementation.

Example 2

Fast High-Resolution Imaging of Clarified Brain Using COLM

Thy1-eYFP mouse brain was perfused with 0.5% acrylamide monomer solution. A 3.15 mm×3.15 mm×5.3 mm volume was acquired from an intact clarified brain using COLM with 25× magnification. The complete image dataset was acquired in ~1.5 hours; for optimal contrast the LUT of zoomed-in images was linearly adjusted between panels. Magnified views from FIG. 3 panel c region defined by rectangles were obtained (FIG. 3, Panels a, b). Maximum-intensity projections of over a 50 micron-thick volume were obtained (FIG. 3, Panels d-i, shown by the progression of boxes and arrows). Camera exposure time of 20 ms was used; refractive index liquid 1.454 was used as the immersion medium.

Example 3

Molecular Interrogation of Clarified Tissue

Whole mouse brain was perfused with 4% acrylamide monomer solution and clarified passively, and immunostained to label all parvalbumin (PV) positive neurons. The intact brain was imaged using COLM with a 25× objective. Labeled cells at different depths in the sample were observed (FIG. 4B).

Figure 4A:
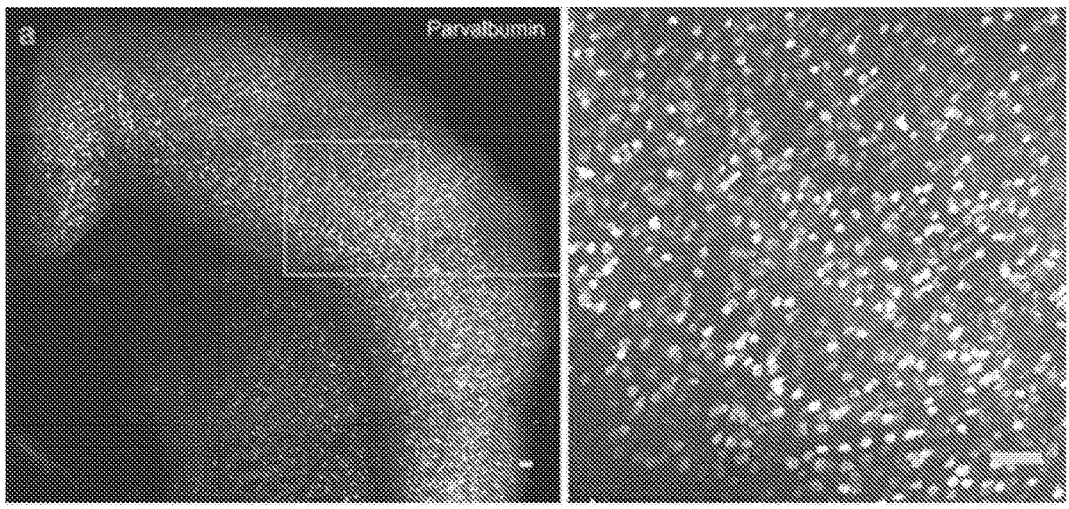
FIGS. 4A-4C show images of parvalbumin immunostaining in clarified intact mouse brain imaged using COLM. The image in FIG. 4B was collected using COLM, while the images in FIG. 4A and FIG. 4C were collected using confocal microscopy. All images represent maximum Z-projections and all scale bars are 100 µm.

CLARITY optimized objectives were used to image clarified mouse brain tissue blocks with a confocal microscope (FIGS. 4A and C). The mouse brain was perfused with 4% acrylamide monomer solution and immunostained with anti-PV antibody. Confocal microscopy with CLARITY optimized water-immersion objectives (10×, 0.6 NA, 3 mm) was used to acquire high quality images of a 1 mm thick tissue block, and the images were processed to generate maximum intensity projection images of PV positive neurons (FIG. 4A).

Figure 4C:
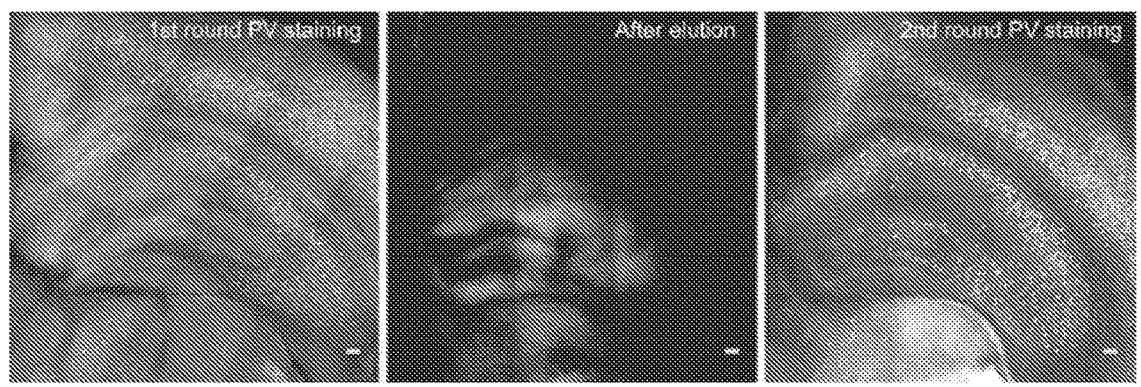

It was also possible to perform multiple rounds of immunostaining and confocal imaging with CLARITY optimized water-immersion objectives (10×, 0.6 NA, 3 mm) in the same tissue block from clarified mouse brain. 1% acrylamide monomer solution was used to perfuse the mouse brain. After the first round of immunostaining for PV (FIG. 4C, left panel), the label was eluted overnight (~12 hours) by incubation in clearing buffer at 60° C. (FIG. 4C, middle panel). The tissue block was subsequently immunostained with anti-PV antibody (FIG. 4C, right panel). DAPI present in the first round was successfully eluted as well. All images shown represent maximum Z-projections.

Example 4

Comparison of Confocal, Two-Photon and Light Sheet Microscopy

Confocal microscopy (FIG. 5, left column) achieves optical sectioning by employing a pinhole in front of the photomultiplier tubes (PMTs). Two-photon microscopy (FIG. 5, middle column) utilizes the fact that only simultaneous absorption of two photons (of longer wavelengths) results in fluorescence signal emission, an event more likely to occur at the point of highest light intensity in the sample i.e. the focal plane. Light sheet fluorescence microscopy (FIG. 5, right column) achieves optical sectioning by selectively confining the illumination to the plane of interest. Confocal and two-photon are point scanning and hence inherently slow, whereas light sheet microscopy uses fast sCMOS/CCD cameras to image the selectively illuminated focal plane, resulting in 2 to 3 orders of magnitude faster imaging speed and minimal photo-bleaching.

The compatibility of clarified samples with light sheet was assessed and greater than 2 orders of magnitude faster imaging speed with minimal photobleaching was achieved; for example, an entire mouse brain was imaged in about 4 hours using a 10× magnification objective and in about 1.5 days using a 25× objective, as opposed to many days and months, respectively, with a confocal microscope. CLARITY optimized light-sheet microscopy (COLM) is especially well suited for interrogation of large tissue samples labeled with transgenic or histochemical approaches. The increased speed of acquisition and higher quality of data generated via CLARITY using new microscopy methods, combined with high-speed CLARITY processing itself enabled by parallelized and efficient tissue transformation protocols described here, together define a versatile and efficient platform for structural and molecular interrogation of large and fully assembled tissues.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A microscope device comprising:
   an illumination beam path that comprises a light source;
   a detection beam path that comprises a camera;
   an optically homogenous sample manipulation component that comprises a sample chamber having a volume;
   a controller;
   a processor; and
   a computer-readable medium comprising instructions that, when executed by the processor, cause the controller to simultaneously:
   acquire a plurality of alignment parameters for a first location in a sample placed in the sample chamber by aligning a first light sheet plane with a first detection focal plane at the first location in the sample and thereby image the first location in the sample with the first aligned light sheet; and
   acquire a plurality of alignment parameters for a second location in the sample placed in the sample chamber by aligning a second light sheet plane with a second detection focal plane at the second location in the sample and thereby image the second location in the sample with the second aligned light sheet,
   wherein the imaged first location and imaged second location in the sample are used to generate a three dimensional image of the sample.

2. The microscope device according to claim 1, wherein the optically homogenous sample manipulation component comprises an xyz-theta sample mount stage.

3. The microscope device according to claim 2, wherein the xyz-theta sample mount stage has a travel range of at least 45 mm in each dimension.

4. The microscope device according to claim 1, wherein the optically homogenous sample manipulation component comprises an inner chamber having a volume that is less than the volume of the sample chamber.

5. The microscope device according to claim 4, wherein the inner chamber is a cuvette.

6. The microscope device according to claim 5, wherein the cuvette comprises fused quartz.

7. The microscope device according to claim 1, wherein the instructions, when executed by the processor, cause the controller to: specify a start position and an end position for a sample in the z-direction, specifying a z-step value, or digitally dividing a sample into a plurality of tiles.

8. The microscope device according to claim 1, wherein the instructions, when executed by the processor, cause the controller to: acquire an alignment parameter for a location within the sample by linear interpolation from two adjacent locations.

9. The microscope device according to claim 1, wherein aligning the light sheet and the detection focal plane comprises maximizing an image quality measurement, wherein the measurement is an optical focus quality measurement comprising a ratio of first frequency and second frequency signals in Fourier space.

10. The microscope device according to claim 1, wherein the imaging procedure comprises:
   aligning a detection focal plane of the microscope with an illumination plane of the sample using an alignment parameter;
   illuminating a linear portion of the illumination plane with the light source; and
   capturing a plurality of emitted light signals along the illuminated linear portion of the illumination plane with the camera.

11. The microscope device according to claim 10, wherein the imaging procedure further comprises:
   directing the light source to illuminate a plurality of different linear portions of the illumination plane; and
   capturing a plurality of emitted light signals along each of the different linear portions of the illumination plane to form a two dimensional image of the sample with the camera.

12. The microscope device according to claim 1, wherein the detection beam path comprises a detection objective having a refractive index that is matched to a refractive index of a sample.

13. The microscope device according to claim 1, wherein the device comprises two illumination beam paths.

14. The microscope device according to claim 13, wherein the device comprises two detection beam paths.

15. The microscope device according to claim 13, wherein the two illumination beam paths are configured to illuminate the sample from opposing sides of the optically homogenous sample manipulation component.

16. A method of imaging a sample using a microscope device, the method comprising:
   placing the sample in a sample chamber in an optically homogenous sample manipulation component;
   simultaneously:
   aligning a first light sheet with a first detection focal plane of a microscope device at a first location within the sample to determine an alignment parameter for the first location and thereby imaging by
   illuminating the first location with the first light sheet to align the first light sheet with the first detection focal plane and capturing a first image of the first location with the first light sheet; and
   aligning a second light sheet with a second detection focal plane of the microscope device at a second location within the sample to determine an alignment parameter for the second location and thereby imaging by illuminating the second location with the second light sheet to align the second light sheet with the second detection focal plane and capturing a second image of the second location with the second light sheet; and
   constructing a three-dimensional image of the sample using the first image and second image.

17. The method according to claim 16, wherein the method comprises simultaneously illuminating two or more different planes of the sample using two or more independent light sheets.

18. The method according to claim 16, wherein the method comprises simultaneously illuminating two different planes of the sample using switching of a single light sheet.

19. The method according to claim 16, further comprising filling the sample chamber with a solution having a refractive index that matches a refractive index of the sample.

20. The method according to claim 16, wherein the method further comprises acquiring an alignment parameter for a location within the sample by linear interpolation from two adjacent locations.

21. The method according to claim 16, wherein aligning the light sheet and the detection focal plane comprises maximizing an image quality measurement, wherein the measurement is an optical focus quality measurement comprising a ratio of first frequency and second frequency signals in Fourier space.

22. The method according to claim 16, wherein the imaging procedure comprises:
   aligning a detection focal plane of a camera with an illumination plane of the sample using an alignment parameter;
   illuminating a linear portion of the illumination plane with the light source; and
   capturing a plurality of emitted light signals along the illuminated linear portion of the illumination plane.

23. The method according to claim 22, wherein the imaging procedure further comprises:
   directing the light source to illuminate a plurality of different linear portions of the illumination plane; and
   capturing a plurality of emitted light signals along each of the different linear portions of the illumination plane to form a two dimensional image of the sample.

* * * * *